United States Patent
Yeager et al.

(10) Patent No.: US 6,825,234 B2
(45) Date of Patent: Nov. 30, 2004

(54) COMPOSITIONS AND METHODS FOR AMELIORATION OF HUMAN FEMALE SEXUAL DYSFUNCTION

(75) Inventors: James L. Yeager, Lake Forest, IL (US); Nadir Büyüktimkin, Robbinsville, NJ (US); Servet Büyüktimkin, Robbinsville, NJ (US)

(73) Assignee: NexMed (Holdings), Inc., Robbinsville, NJ (US)

( * ) Notice: Subject to any disclaimer, the term of this patent is extended or adjusted under 35 U.S.C. 154(b) by 36 days.

(21) Appl. No.: 10/188,554

(22) Filed: Jul. 2, 2002

(65) Prior Publication Data

US 2003/0129241 A1 Jul. 10, 2003

Related U.S. Application Data

(63) Continuation-in-part of application No. 09/208,965, filed on Dec. 10, 1998, now Pat. No. 6,486,207.

(51) Int. Cl.[7] ...................... A61K 31/557; A61K 47/00; A61L 2/16

(52) U.S. Cl. ............... 514/573; 514/772; 514/772.6; 514/777; 514/782; 514/785; 514/817; 514/929; 514/946; 514/947; 514/967; 514/970; 514/974; 514/975

(58) Field of Search ............... 514/573, 772, 514/772.6, 777, 782, 785, 817, 929, 946, 947, 967, 970, 974, 975

(56) References Cited

U.S. PATENT DOCUMENTS

| | | | |
|---|---|---|---|
| 3,069,322 A | 12/1962 | Bergstrom et al. | |
| 3,545,439 A | 12/1970 | Duncan | |
| 3,639,561 A | 2/1972 | Gordon et al. | |
| 3,852,465 A | 12/1974 | Kirton et al. | |
| 4,005,221 A | 1/1977 | Karim | |
| 4,043,339 A | 8/1977 | Roseman | |
| 4,198,405 A | 4/1980 | Enomoto et al. | |
| 4,217,360 A | 8/1980 | Vorbrüggen et al. | |
| RE30,439 E | 11/1980 | Sokolowski | |
| 4,254,145 A | 3/1981 | Birnbaum | |
| 4,289,785 A | 9/1981 | Wilks | |
| 4,311,707 A | 1/1982 | Birnbaum et al. | |
| 4,317,447 A | 3/1982 | Williams | |
| 4,318,908 A | 3/1982 | Enomoto et al. ............ 424/243 |
| 4,352,790 A | 10/1982 | Johansson et al. | |
| 4,472,376 A | 9/1984 | Kamishita | |
| 4,515,810 A | 5/1985 | Chow et al. | |
| 4,557,934 A | 12/1985 | Cooper | |
| 4,680,312 A | 7/1987 | Johnson | |
| 4,771,004 A | 9/1988 | Higuchi | |
| 4,801,587 A | 1/1989 | Voss et al. | |
| 4,820,732 A | 4/1989 | Shell et al. | |
| 4,861,764 A | 8/1989 | Samour et al. | |
| 4,889,845 A | 12/1989 | Ritter et al. | |
| 4,955,878 A | 9/1990 | See et al. | |
| 4,980,378 A | 12/1990 | Wong et al. | |
| 5,059,603 A | 10/1991 | Rubin | |
| 5,082,866 A | 1/1992 | Wong et al. | |
| 5,208,031 A | * 5/1993 | Kelly ..................... 424/412 |
| 5,219,885 A | 6/1993 | Frolich et al. | |
| 5,242,391 A | 9/1993 | Place et al. | |
| 5,324,746 A | 6/1994 | McKee et al. | |
| 5,380,760 A | 1/1995 | Wendel et al. | |
| 5,464,868 A | 11/1995 | Frolich et al. | |
| 5,480,648 A | 1/1996 | Wendel et al. | |
| 5,491,171 A | 2/1996 | Nishimura et al. ......... 514/558 |
| 5,565,466 A | 10/1996 | Gioco et al. | |
| 5,661,178 A | 8/1997 | Chen et al. | |
| 5,698,589 A | 12/1997 | Allen | |
| 5,708,031 A | 1/1998 | Scott ..................... 514/573 |
| 5,773,457 A | 6/1998 | Nahoum | |
| 5,820,587 A | 10/1998 | Place | |
| 5,843,961 A | 12/1998 | Kock et al. | |
| 5,877,216 A | 3/1999 | Place et al. | |
| 5,891,915 A | 4/1999 | Wysor et al. | |
| 5,908,853 A | 6/1999 | Nahoum | |
| 5,952,361 A | 9/1999 | Dias Nahoum | |
| 5,962,528 A | 10/1999 | Scott ..................... 514/573 |

(List continued on next page.)

FOREIGN PATENT DOCUMENTS

| | | |
|---|---|---|
| EP | 0266968 | 5/1988 |
| EP | 0346297 | 12/1989 |
| EP | 0357581 | 3/1990 |
| EP | 0 357 581 B2 | 3/1990 |
| EP | 0432199 | 7/1993 |
| EP | 0 661 052 A1 | 7/1995 |
| JP | 55073676 | 6/1980 |
| JP | 55089297 | 7/1980 |
| JP | 63-135333 | 6/1988 |
| JP | 2-264725 | 10/1990 |
| JP | 5032551 | 2/1993 |
| WO | WO 91/16021 | 10/1991 |
| WO | WO 93/00894 | 1/1993 |
| WO | WO 94/04120 | 3/1994 |
| WO | 94/04120 | * 3/1994 |

(List continued on next page.)

OTHER PUBLICATIONS

STN/CAS online, file MEDLINE, Acc. No. 85025590, (Hoon, Clinical Obstretics and Gynecology (1984), 27 (3), pp. 767–780), Abstract.*

(List continued on next page.)

*Primary Examiner*—Thurman K. Page
*Assistant Examiner*—Frank Choi
(74) *Attorney, Agent, or Firm*—Bowditch & Dewey, LLP

(57) ABSTRACT

The invention provides compositions and methods suitable for ameliorating female sexual dysfunction, and in particular, female sexual arousal disorder. In one embodiment, the invention provides a semisolid composition suitable for topical application comprising: an effective amount of a vasoactive prostaglandin, a polysaccharide thickener, a lipophilic component, and an acidic buffer system.

31 Claims, 10 Drawing Sheets

U.S. PATENT DOCUMENTS

| | | | |
|---|---|---|---|
| 5,981,593 A | 11/1999 | Scott | 514/573 |
| 6,004,578 A * | 12/1999 | Lee et al. | 424/448 |
| 6,017,520 A | 1/2000 | Synodis et al. | |
| 6,031,002 A | 2/2000 | Wysor et al. | |
| 6,036,977 A | 3/2000 | Drizen et al. | |
| 6,046,240 A | 4/2000 | See | |
| 6,046,244 A * | 4/2000 | Buyuktimkin et al. | 514/785 |
| 6,251,436 B1 | 6/2001 | Drizen et al. | 424/488 |
| 6,291,528 B1 | 9/2001 | Scott | 514/573 |
| 6,294,550 B1 | 9/2001 | Place et al. | 514/302 |
| 6,403,658 B1 | 6/2002 | Toppo | 514/929 |
| 6,486,207 B2 * | 11/2002 | Yeager et al. | 514/573 |
| 2001/0022975 A1 | 9/2001 | Drizen et al. | 424/486 |
| 2001/0051656 A1 | 12/2001 | Place et al. | 514/530 |

FOREIGN PATENT DOCUMENTS

| | | |
|---|---|---|
| WO | WO 95/11683 | 5/1995 |
| WO | WO 98/50039 | 11/1998 |
| WO | WO 99/20266 | 4/1999 |
| WO | WO 99/22714 | 5/1999 |
| WO | WO 99/22731 | 5/1999 |
| WO | WO 99/30718 | 6/1999 |
| WO | WO 99/56741 | 11/1999 |
| WO | WO 00/33825 | 6/2000 |
| WO | WO 00/69469 | 11/2000 |
| WO | WO 01/51053 A1 | 7/2001 |
| WO | WO 01/74279 A1 | 10/2001 |
| WO | WO 03/022310 A1 | 3/2003 |

OTHER PUBLICATIONS

STN/CAS online, file EMBASE, Acc. No. 1998207596 (Leiblum, International Journal of Impotence Research (1998), 10/Suppl. 2, S104–S106), Abstract.*

Buyuktimkin et al., The utility of biodegradable penetration enhancers, dodecyl 2–(N,N–dimethylamino)–proprionate (DDAIP) and 2–(N,N–dimethylamino)–propanol tetradecanoate (DAIPM),(Pharm. Res. ,14, No. 11, Supp., S451, 1997), STN/CAS online, file DRUGU, abstract.*

Büyüktimkin et al., The Utility of Biodegradable Penetration enhancers, dodecyl 2–(N,N–dimethylamino)–proprionate (DDAIP) and 2–(N,N–dimethylamino)–propanol tetradecanoate (DAIPM), (Pharm. Res., 14, No. 11, Supp., S451, 1997), STN/CAS online, file DRUGU, abstract.

Neibergall, P.J., "Ionic Solutions and Electrolytic Equilibrai." In *Remington: The Science and Practice of Pharmacy*, A.R. Gennaro, et al., eds. (Lippincott, Williams & Wilkens), 17:227–245 (2000).

STN/CAS online, file MEDLINE, Acc. No. 85025590, (Hoon, Clinical Obstetrics and Gynecology (1984), 27 (3), pp. 767–780), Abstract.

STN/CAS online, file EMBASE, Acc. No. 1998207596 (Leiblum, International Journal of Impotence Research (1998), 10/Suppl. 2, S104–S106), Abstract.

Foldvari, M., et al., "Transcutaneous Delivery of Prostaglandin $E_1$: In Vitro and Laser Doppler Flowmetry Study," Journal of Pharmaceutical Sciences, vol. 87, No. 6, 721–725 (Jun. 1998).

Phillips, N., et al. (1999) "A Vaginal Plethysmography Pilot Study to Investigate the Efficacy and Safety of Placebo and Three Different Doses of Topical Alprostadil USP (Prostaglandin $E_1$) Cream in Female Patients with Sexual Dysfunction," Copy of presentation at meeting "New Perspectives in the Management of Female Sexual Dysfunction" Oct. 22–24, 1999, Boston, MA.

Akkus, E., et al., Duplex ultrasonography after prostaglandin E1 injection of the clitoris in a case of hyperreactio luteinalis, *J. Urol.* 153: 1237–38 (1995).

Basson, R., et al., Report of the international consensus development conference on female sexual dysfunction: definitions and classifications, *J. Urol.* 163: 888–93 (2000).

Berman, J.R., et al., Clinical evaluation of female sexual function: effects of age and estrogen status on subjective and physiologic sexual responses, *Int. J. Impotence Research* 11: S31–38 (1999).

Deamer, R.L. and Thompson, J.F., The role of medicaitons in geriatric sexual function, *Geriatric Sexuality* 7: 95–111 (1991).

Holzapfel, S., Sexual medicine in family practice, *Can. Fam. Physician* 39: 618–20, 623–24 (1993).

Howard, J.R., The management of common sexual problems in general practice, *Modern Medicine of Australia*: 78–81, 84–88 (1996).

Kim, E.D. and McVary K.T., Topical prostaglandin–E1 for the treatment of erectile dysfunction, *J. Urol.* 153: 1828–30 (1995).

Leffler, C.W. and Amberson, J.I., Intravaginal prostaglandin $E_1$ increases vaginal blood flow, *Prostagl., Leukotrienes Med.* 9: 587–89 (1982).

Leiblum, S.R., What every urologist should know about female dysfunction, *Int. J. Impotence Research* 11: S39–S40 (1999).

McKenna, K., The brain is the master organ in sexual function: Central nervous system control of male and female sexual function, *Int. J. Impotence Research* 11: S48–S55 (1999).

Uttley, L., Treatment of sexual dysfunction, *Peritoneal Dialysis Int.* 16: S402–05 (1996).

Wolfson, B., et al., Intraurethral prostaglandin E–2 cream: A possible alternative treatment for erectile dysfunction, *Urology* 42: 73–75 (1993).

Büyüktimkin, N., et al., Chemical Means of Transdermal Drug Permeation Enhancement, in Gosh, T.K., et al., (eds) *Transdermal and Topical Drug Delivery Systems*, Interpharm Press, Inc., Buffalo Grove, IL (1997).

Büyüktimkin, N., et al., Alkyl N,N–Disubstituted–Amino Acetates, in Smith, E.W., et al., (eds) *Percutaneous Penetration Enhancers*, CRC Press, Inc., (1995).

Catanzarite, Valerian A. and Gary Aisenbrey, *Contemporary OB/GYN* (Oct. 1987).

Chattaraj, S.C. and Walker, R.B., Penetration Enhancer Classification, pp. 5–20 in Maibach, H.I., and Smith, H.E., (eds). *Percutaneous Penetration Enhancers*, CRC Press, Inc., Boca Raton, FL (1995).

Davidson R. L., *Handbook of Water–Soluble Gums & Resins*, McGraw–Hill, Inc., N.Y. (1980).

Derogatis, L.R. and Conklin–Powers, B., Psychological assessment measures of female sexual functioning in clinical trials, *Int. J. Impot. Res.* 10 Suppl. 2: S111–S116 (1998).

Goldstein, I., and Berman, J.R. Vasculogenic female sexual dysfunction: vaginal engorgement and clitoral erectile insuffciency syndromes, *Int. J. Impotence Research* 10: Suppl. 2, S84–S90 (1998).

Goldstein, M. K. et al., Gynecological factors in sexual dysfunction of the older woman. *Clin. Geriatr. Med.* 7: 41–61, (1991).

Graf, A.H., et al., Helospectin and pituitary adenylate cyclase activating polypeptide in the human vagina, *Regul. Pept.* 55: 277 (1995).

Heiman, J. R. and Meston, C. M., Empirically validated treatment for sexual dysfunction. *Annual Review of Sex Research*, 8: 148–194 (1997).

Hilliges, M. et al., Innervation of the human vaginal mucosa as revealed by PGP 9.5 immunohistochemistry, *Acta Anatomica* 153: 119 (1995).

Kabadi, M.B., and Chien, Y.W., Intravaginal controlled administration of Flurogestone acetate. II: Development of an in vitro system for studying the intravaginal release and permeation of Flurogestone acetate, *J. Pharm. Sci.* 73: 1464–1468 (1984).

Laan, E., et al., Determinants of subjective experience of sexual arousal in women. Feedback from genital arousal and erotic stimulus content, *Psychophysiol,* 32: 444–51 (1995).

Laumann, E. O., et al, Sexual dysfunction in the United States. *JAMA* 281:537–544 (1999).

Lee, K.C., et al., Simultaneous determination of prostaglandins $E_1$, $A_1$ and $B_1$ by reversed–phase high–performance liquid chromatography for the kinetic studies of prostaglandin $E_1$ in solution, J. Chromatography, 555 (1991) 73–80.

Lehninger, Albert L., *Biochemistry*, 2d ed. (1975), pp. 300, 686–87.

Meuwissen and Over, Habituation and Dishabituation of Female Sexual Arousal, *Bahav. Res. Ther.* 28: 217–26 (1990).

Palace, E.M. and Goralka, B.B., Differential patterns of arousal in sexually functional and dysfunctional women: Physiological and subjective components of sexual respones, *Arch. Sexual Behav.* 21: 135–159 (1992).

Remington's Pharmaceutical Sciences 19th Edition, 1995, A. R. Gennaro, Ed., Mack Publishing Company, Easton, Pa, pp. 410–12.

Rosen, R. C. and Leiblum, S. R., Treatment of sexual disorders in the 1990s: an integrated approach. *Journal of Consulting and Clinical Psychology* 63: 877–890 (1995).

Sadeghi–Nejad, H., et al., Impotence is a couple's disease: studies in female sexual dysfunction, *J. Urol* 155: 677A, (1996).

Shaaf, T.K. and Corey, E.J., A Total Synthesis of Prostaglandins $F_{1a}$ and $E_{1i}$ J. Org. Chem. 37:2921–22 (1972).

Sipski, M. L. et al., Physiological parametrs associated with psychogenic sexual arousal in women with complete spinal cord injuries. *Arch Phys Med Rehabil* 76: 811–818 (1995).

Slob, A. K., et al., Sexuality and psychophysiological functioning in women with diabetes mellitus, *J Sex Marital Ther.* 59–69 (1990).

Spector, I. P. and Carey, M. P., Incidence and prevalence of the sexual dysfunctions: a critical review of the empirical literature. *Archives of Sexual Behavior* 19: 389–407 (1990).

Taylor, J. F., et al., Self–report assessment of female sexual function: psychometric evaluation of the Brief Index of Sexual Functioning for Women, *Arch. Sexual Behav.* 23: 627–643 (1994).

* cited by examiner

COMPOSITIONS AND METHODS FOR AMELIORATION OF HUMAN FEMALE SEXUAL DYSFUNCTION

RELATED APPLICATIONS

This application is a continuation-in-part of application Ser. No. 09/208,965, filed Dec. 10, 1998, now issued U.S. Pat. No. 6,486,207, which is related to International Application No. PCT/US99/29471, filed Dec. 10, 1999, the disclosures of which are hereby incorporated herein in their entirety.

BACKGROUND OF THE INVENTION

Sexual dysfunction has been a persistent problem, more frequent in an aging population, that has only recently been addressed with frank evaluation, scientific investigation and effective treatment. Male impotence, especially male erectile dysfunction, has received the most attention. Female sexual dysfunction has been considered in the context of male erectile dysfunction, in part because of the anatomical and physiological parallels between the male and female genitalia, and in part, with the hope that effective treatments for male erectile dysfunction could provide some relief for female sexual dysfunction.

Both male and female sexual behavior is viewed from the standpoint of a four-phase sexual response cycle consisting of the stages of desire, excitement, orgasm and resolution. Studies have shown that while there are many similarities between male and female sexual response, significant differences exist. Specific dysfunctions have been correlated with the phases of the model. The female sexual response and its dysfunctions remain poorly understood.

Female sexual arousal disorder (FSAD) is the persistent or recurrent inability to attain, or to maintain, sufficient sexual excitement, which causes personal distress. It may be expressed as lack of subjective excitement, lack of genital response, such as lubrication and swelling, or lack of other somatic responses. Female sexual arousal disorder is one form of female sexual dysfunction, and is associated with the excitement phase.

While increased understanding of the pathophysiology of male erectile dysfunction has progressed rapidly in the past decade and led to new therapeutic modalities, little has been done to address similar issues in women. Cardiovascular risk factors have been shown to correlate with complaints of vaginal and clitoral dysfunction. Goldstein, M. K., et al.,: Gynecological factors in sexual dysfunction of the older woman. *Clin Geriatr Med* 7: 41–61, (1991); Sadeghi-Nejad, H., et al.: Impotence is a couple's disease: studies in female sexual dysfunction. *J Urol* 155: 677A, (1996); Slob, A. K., et al.: Sexuality and psychophysiological functioning in women with diabetes mellitus. *J Sex Marital Ther:* 59–69, (1990).

The correlation of cardiovascular risk factors and complaints of vaginal and clitoral dysfunction have led to suggestions that a significant degree of female sexual dysfunction is due to vascular insufficiency and therefore amenable to treatment with vasoactive agents. The underlying foundations of the normal and dysfunctional female sexual response must be considered in the context of the anatomy and physiology, summarized below. See, generally, Goldstein, I., and Berman, J. R., Vasculogenic female sexual dysfunction: vaginal engorgement and clitoral erectile insufficiency syndromes, *Int. J. Impotence Research* 10: Suppl. 2, S84–S90 (1998).

Anatomy of the Vagina

The vagina is the canal that connects the uterus with the external genital organs. Its design easily accommodates penetration of a rigid penile erection. At the posterior end the rounded neck of the uterus, the cervix, projects into the space known as the fornix or vaginal vault. Anteriorly, two pleats of sensitive tissue, the labia minora, surround the opening of the vagina and are further protected by larger folds known as the labia majora.

The walls of the vagina consist of three layers—an inner mucosa, an aglandular mucous membrane epithelium, an intermediate, highly vascularized muscularis layer, and an outer supportive fibrous mesh. The vaginal mucosa is a mucous type stratified squamous cell epithelium that undergoes hormone-related cyclical changes, such as a slight keratinization of the superficial cells during the menstrual cycle. The muscularis portion comprises smooth muscle and an extensive arborization of blood vessels that may swell during intercourse. The surrounding fibrous layer provides structural support to the vagina; this layer consists of elastin and collagen fibers that allow for expansion of the vaginal vault during sexual arousal or childbirth. Large blood vessels run within the mucosa, and nerve plexuses are present within muscular and adventitial layers. The vagina has many rugae or folds that are necessary for the distensibility of the organ during intercourse and childbirth. Smaller ridges lend to the frictional tension that exists during intercourse.

The arterial supply to the vagina is derived from an extensive network of branching vessels surrounding it from all sides. The anterior branch of the internal iliac artery continually bifurcates as it descends through the pelvis with a series of the newly generated vessels, each supplying the vagina to some degree. After giving off an obturator artery branch, the umbilical, and the middle rectal arteries diverge off to supply a superior and inferior vesical artery, respectively. Between the umbilical and the mid-rectal branches there is a generation of a uterine artery, which further bifurcates to give the vaginal artery. The internal pudendal and accessory pudendal artery also send a branch to the vaginal artery. Finally, the common clitoral artery sends a branch to the vaginal muscularis.

The neurologic innervation of the vagina originates from two separate plexuses, the superior hypogastric plexus and the sacral plexus, The hypogastric nerve plexus descends on the great vessels spreading into an inferior hypogastric plexus, which systematically branches further into a uterovaginal nerve. The somatic pudendal nerve originates off the pelvic splanchnic branches from the secret plexus. Pudendal branching innervates the vagina towards the opening of the introitus as the perineal and posterior labial nerves.

Immunohistochemistry studies have been utilized to better understand the innervation of the human vaginal mucosa. In a study by Hilliges et al. using protein gene product 9.5, more distal areas of the vagina had significantly more nerve fibers compared to the more proximal parts, and the anterior wall showed a denser innervation than the posterior wall (Hilliges, M. et al., Innervation of the human vaginal mucosa as revealed by PGP 9.5 immunohistochemistry, *Acta Anatomica* 153: 119 (1995)). Graf et al studied the distribution patterns and the occurrence of helospectin and pituitary adenylate cyclase activating polypeptide (PACAP) immunoreactivity (Graf, A. H., et al. Helospectin and pituitary adenylate cyclase activating polypeptide in the human vagina, *Regul. Pept.* 55: 277 (1995)). They confirmed a dense network of vasoactive intestinal peptide (VIP) immunoreactive nerve fibers showing sub-populations of helospectin and LI-type PACAP. Nerve fibers of the vagina had previously been shown to be active in association with specific peptides that include VIP, peptide histidine methionine (PHM), calcitonin gene related peptide (CGPP), and galanin. Genital vasodilation and subsequent increase in vaginal blood flow and lubrication have been observed upon exposure of vessels to VIP. VIP has been implicated as the neurotransmitter for mediating vaginal vasodilation and the formation of lubricating fluid during sexual arousal. Helospectin and PACAP, a potent vasodilator, belong to the same peptide family as VIP and PHM, and recent observations have been made to the effect that distributions and co-localizations of helospectin and VEP as well as PACAP and VIP have been reported in the mammalian gastrointestinal tract.

The vaginal canal is lubricated primarily from a transudate originating from the subepithelial vascular bed passively transported through the interepithelial spaces, sometimes referred to as intercellular channels. Additional moistening during intercourse comes from secretion of the paired greater vestibular or Bartholin's glands.

Estrogen effects on the maintenance and function of female genitalia have been well documented in studies. Estrogen receptors have been shown to exist throughout the vaginal epithelium, in stromal cells, and in the smooth muscle fibers in the muscularis. Weaker conformations of estrogen such as estriol appear more effective in stimulating the vagina as opposed to the uterus. Thickness and rugae of the vaginal wall, as well as vaginal lubrication, have been shown to be estrogen dependent. Although this fluid production has been shown to be hormone-dependent both in the resting state and during sexual excitement, quantitative changes apparently do not occur during the menstrual cycle. An insufficient amount of estrogen will result in thin vaginal walls more easily susceptible to trauma with a decreased ability to heal, as well as a drier and less acidic vaginal environment more vulnerable to infection. Vaginal dryness is associated with ovarian failure and is effectively controlled by estrogen replacement therapy. Some women who are not sexually active may not notice the extent of vaginal atrophy but when coitus does resume, pain and discomfort from intercourse can be considerable.

Anatomy of the Clitoris

The clitoris is the homologue of the penis arising from the embryological genital tubercle. The clitoris consists of a cylindrical, erectile organ composed of three parts: the outermost glans or head, the middle corpus or body, and the innermost crura. The glans of the clitoris is visualized as it emerges from the labia minora, which bifurcate to form the upper prepuce anteriorly and the lower fronulum posteriorly. The body of the clitoris consists of two paired corpora cavernosa of about 2.5 cm in length and lacks a corpus spongiosum. The body extends under the skin at the corona to the crura. The two crura of the clitoris, formed from the separation of the most proximal portions of the corpora in the perineum, attach bilaterally to the undersurface of the symphysis pubis at the ischiopubic rami.

A fibrous tunica albuginea ensheathes each corporal body made up of lacunar space sinusoids surrounded by trabecula of vascular smooth muscle and collagen connective tissue. No retractor clitoridis muscle exists in humans as it does in other animals such as cattle and sheep, however a supporting suspensory ligament does hold the clitoris in the introital region.

The main arterial supply to the clitoris is from the illo-hypogastric-pudendal arterial bed. The internal pudendal artery is the last anterior branch off the internal iliac artery. Distally, the internal pudendal artery traverses Alcock's canal, a position of the obturator fascia and lies on the inner side in apposition to the ischio-pubic ramus. In this latter location, the artery is susceptible to blunt perineal trauma. The internal pudendal artery terminates as it supplies the inferior rectal and perineal artery, which supplies the labia. The common clitoral artery continues to the clitoris. This artery bifurcates into a dorsal clitoral artery and a cavernosal clitoral artery.

Autonomic efferent innervation of the clitoris passes from the pelvic and hypogastric nerves to the clitoris through the urogenital diaphragm. Pelvic nerve stimulation results in clitoral smooth muscle relaxation and arterial smooth muscle dilation. There is a rise in clitoral cavemosal artery inflow, an increase in clitoral intracavemous pressure which lead to tumescence and extrusion of the glans clitoris.

Anatomical studies using female rats have indicated that the major neuronal input to the clitoris was seen in spinal segments from L5-S1, and to a lesser extent in T12-L4 as well as S2-S4. When a label that is taken up by nerve terminals and transported retrogradely to the nerve cell bodies (pseudorabies virus) was injected into the clitoris, labeled nerve cell bodies were found in the brain in multiple locations, including the nucleus paragigantocellularis, raphe pallidus, raphe magnus, Barrington's nucleus, ventrolateral central gray, hypothalamus, and the medial pre-optic region. This implies a multisynaptic circuit of neurons may be involved in clitoral neurological control rather than just a simple somatic reflex connection.

Morphological studies have been performed using wheat germ agglutinin conjugated with horseradish peroxidase (WGA/HRP) injected into the clitoris of the female cat to compare afferent pathways to the entire population of pudendal nerve afferents. Central projections of the clitoral afferents were identified in the L7-S3 segments with the most prominent labeling in S1-S2. In the same study, electrophysiological analysis of the clitoris performed under constant mechanical pressure stimulation indicated both phasic and tonic discharges in L7-S2, but most prominently in S1. In contrast electrical stimulation of the clitoris evoked discharges at S1 only. The neurotransmitters mediating clitoral and arterial smooth muscle dilation remain undetermined, however preliminary studies suggest that nitric oxide is involved. Histochemical studies have revealed VIP and neuropeptide Y (NPY) immunoreactive nerves in the clitoral erectile tissues. Somatic sensory pathways originate from the clitoral skin. There exists a dense collection of Pacinian corpuscles innervated by rapidly adapting myelinated afferents, as well as Meissner's corpuscles, Merckel tactile disks, and free nerve endings. These sensory afferents pass from the dorsal clitoral nerve to the pudendal nerve.

Physiology of Female Sexual Arousal

The female sexual response phase of arousal is not easily distinguished from the phase of desire until physiological changes begin to take place in the vagina and clitoris as well as other sexual organs. Sexual excitement and pleasure are accompanied by pelvic vasocongestion and swelling of the external genitalia including vaginal engorgement and clitoral erection.

Vaginal engorgement enables a process of plasma transudation to occur, allowing a flow through the epithelium and onto the vaginal surface. Plasma transudation results from the rising pressure in the vaginal capillary bed during the arousal state. In addition there is an increase in vaginal length and luminal diameter, especially in the distal $2/3$ of the vaginal canal.

Dissociation Of Genital Reflexes From Subjective Arousal

Central nervous system areas primarily implicated in sexual arousal, based on animal research, include the medial preoptic, anterior hypothalamic region and related limbic-hippocampal structures. Cognitive effects have been investigated, and in one study the results suggest that the greatest contribution to sexual arousal in the female results from cognitive processing of stimulus content and meaning, and not from peripheral vasocongestive feedback (Laan, E., et al., Determinants of subjective experience of sexual arousal in women. Feedback from genital arousal and erotic stimulus content, *Psychophysiol.* 32: 44-(1995)).

The distinction between local physiological aspects of sexual response, such as genital vasocongestion measured by vaginal photoplesmography, and subjective sexual arousal, measured by self-reporting rating scales and inventories has been clearly demonstrated in both normal and sexually dysfunctional women (Palace, E. M. and Goralka, B. B., Differential patterns of arousal in sexually functional and dysfunctional women: Physiological and subjective components of sexual response, *Arch. Sexual Behav.* 21: 135–159 (1992)). Several reliable and validated self-report inventories are recognized for measurement of female sexual function (Derogatis, L. R. and Conklin-Powers, B., Psychological assessment measures of female sexual functioning in clinical trials, *Int. J. Impot. Res.* 10 Suppl. 2:S111–S116 (1998)).

There does not appear to be a relation between menstrual phases and physiologic arousability. Meuwissen and Over (Habituation and Dishabituation of Female Sexual Arousal, *Behav. Res. Ther.* 28: 217-(1990)) have found that neither film-induced nor fantasy-induced levels of sexual arousal varied significantly throughout the menstrual cycle. There are conflicting reports as well as to the habituation of the female sexual response. Some claim that levels of subjective and physiologic sexual arousal decrease over repeated exposure to sexual stimuli. Others could not elucidate similar results even after 21 trials, yet both concur that the subsequent presentation of a novel stimulus will increase the female sexual response. The desire for increased sexual performance on sexual arousal in functional women have been found to facilitate genital responses, most prominently with the stimulus of erotic fantasy as opposed to erotic film. Interestingly, masturbation frequency had no affect on genital responses despite its significance on subjective reports of arousal. (Laan et al, 1995; Meuwissen and Over, 1990).

Clinicians and researchers have assumed that sexual arousal, is inhibited by the sympathetic nervous system, while facilitation and maintenance are through the parasympathetic nervous system. However, studies have challenged these notions in the woman. Intense exercise, consisting of twenty-minute bike riding sessions, increased physiological sexual arousal measured by vaginal photoplethysmography. This challenged the notion that sympathetic nervous system stimulation inhibited sexual arousal in women and further provided evidence that sexual arousal was actually facilitated by the sympathetic nervous system. Another study examined the temporal effect of sympathetic activation through acute exercise on immediate delayed, and residual sexual arousal. Sexual arousal was objectively assessed by vaginal plethysmography. A relationship between sympathetic nervous system activation and sexual arousal was found, such that sexual arousability was inhibited five minutes post-exercise and was facilitated fifteen minutes post-exercise and only marginally increased thirty minutes post-exercise. The two studies suggest that sympathetic nerve stimulation activation plays an important facilitatory role in the early stages of sexual arousal.

The clitoris may play a major role during sexual activity in that it is not only part of what makes the sexual act enjoyable for the woman but also enhances her response to coitus upon clitoral stimulation. Clitoral stimulation may induce local autonomic and somatic reflexes causing vaginal vasocongestion, engorgement, and subsequent transudation, lubricating the introital canal making the sexual act easier, more comfortable, and more pleasurable. The more stimulation, the higher the level of arousal and the easier it is to further increase stimulations.

Vasculogenic Female Sexual Dysfunction

Female sexual dysfunction has traditionally included disorders of desire/libido, disorders of arousal, pelvic pain disorders, and inhibited orgasm. Patient surveys estimate that 18–76% of adult women have such complaints during sexual activity. Female sexual dysfunction which may have its origin in abnormal arterial circulation into the vagina or clitoris during sexual stimulation, usually from atherosclerotic vascular disease may be considered a disorder of arousal. This vasculogenic female sexual dysfunction may include such clinical symptoms as delayed vaginal engorgement, diminished vaginal lubrication, pain or discomfort with intercourse, diminished vaginal sensation, diminished vaginal orgasm, diminished clitoral sensation or diminished clitoral orgasm. Traumatic injury to the ilio-hypogastric-pudendal arterial bed from pelvic fractures or blunt perineal trauma may also result in diminished vaginal/clitoral blood flow following sexual stimulation and fall into this vasculogenic category.

Prostaglandins

The prostaglandins are a series of cyclic derivatives of certain unsaturated fatty acids. They are found in a variety of tissues, including the prostate gland, the seminal vesicles, the lungs and the brain. These naturally occurring prostaglandins are derived by cyclization of 20-carbon unsaturated fatty acids such as arachidonic acid. See Lehninger, Albert L., *Biochemistry,* 2d ed. (1975), p. 300 (hereinafter "Lehninger").

Prostaglandins as a class of compounds have diverse pharmacologic activity, including stimulation of gastrointestinal and reproductive smooth muscle, relaxation and contraction of respiratory smooth muscle, hypotensive activity, inhibition of fatty acid lipolysis, inhibition of blood platelet aggregation, and inhibition of gastric acid secretion. Therapeutic utility of prostaglandins in general is correspondingly broad. As for prostaglandin $E_1$("$PGE_1$")in particular, this compound, salts thereof, and lower alkyl esters thereof are well known and disclosed, e.g., in U.S. Pat. Nos. 3,069,322 (Bergstrom et al.), 5,219,885 (Froelich et al.) and in J. Org. Chem. 1974, 37, 2921. $PGE_1$ has found utility in the treatment of peripheral occlusive diseases, acute myocardial infarction, angina pectoris, acute ischemic stroke, asthma, gastrointestinal ulcers, ulcers of the skin, and organ rejection. Various routes of administration have been described, including oral, intravenous, buccal, rectal, intra-arterial, subcutaneous, and sublingual. The preferred route of administration of $PGE_1$ will of course be dependent on the particular intended therapeutic use.

Prostaglandins are well known to those skilled in the art. This class of drugs includes those derivatives of prostanoic acid (5-octylcyclopentaneheptanoic acid) referred to as A-I series prostaglandins. Prostaglandin nomenclature is well known and disclosed, e.g., in page 409, Remington's Pharmaceutical Sciences, 18th Edition, 1990, A. R. Gennaro, Ed., Mack Publishing Company, Easton, Pa. The term "prostaglandin" as used generically herein refers to the prostaglandin free acid and pharmaceutically acceptable derivatives thereof, including $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$, carboprost tromethamine, dinoprost tromethamine, dinoprostone, lipoprost, gemeprost, metenoprost, sulprostone and tiaprost as well as salts and esters thereof. Preferred prostaglandins for use in the formulations of this invention include those prostaglandins comprising a β-hydroxyketone moiety, including D-series and E-series prostaglandins, preferably E-series prostaglandins such as prostaglandin $E_1$, including pharmaceutically acceptable salts and lower alkyl esters thereof (the term "lower alkyl" as used herein means straight chain or branched chain alkyl containing one to four carbon atoms). Of the lower alkyl esters, the ethyl ester of prostaglandin $E_1$(commercially available from Sigma Chemical Company, St. Louis, Mo., and preparable as disclosed, e.g., in U.S. Pat. No. 5,219,885, incorporated herein by reference) is preferred.

The biosynthesis of prostaglandins has been well characterized. See, e.g., Lehninger at p. 687. In a typical biosynthetic pathway, exemplified by production of $PGE_2$, the essential fatty acid linoleic acid is converted into the 20-carbon arachidonic acid, which is then acted upon by prostaglandin synthase, a dioxygenase enzyme. Oxygen atoms are added at carbon atoms 9 and 15, and the product is cyclized by formation of a bond between carbon atoms 8 and 12. In the presence of reduced glutathione, this cyclized product undergoes conversion into prostaglandin $PGE_2$. Other types of naturally occurring prostaglandins are derived from different polyunsaturated fatty acids.

In about the 1960s, prostaglandins were isolated from a particular species of Caribbean coral, which made them more widely available for research. Catanzarite, Valerian A. and Gary Aisenbrey, *Contemporary OB/GYN* (October 1987), p. 22. A large number of natural and synthetic analogues of the prostaglandins are now known. Lehninger at 687.

The prostaglandins are known to produce often unpredictable effects over a very wide range of biological activities of a hormonal or regulatory nature. Prostaglandins have been reported to both lower and raise blood pressure, to inhibit gastric secretion, dilate bronchi, inhibit lipolysis, antagonize vasopressin-induced anti-diarrhesis, constrict the pupil, increase and decrease the intraocular pressure and produce contraction of the uterus. See, e.g., Ganong, William F., *Review of Medical Physiology*, 7th ed. (1975), p. 226 (hereinafter "Ganong"). The naturally occurring prostaglandins all appear to be capable of affecting the control of vascular and other smooth muscle contractions. In the central nervous system, prostaglandins are known to modify responses to certain synaptic transmitters. They have been reported to mimic the actions of some hormones and to inhibit the actions of certain others. See Ganong at 226.

Two of the most extensively studied of the prostaglandins are $PGE_2$ and $PGF_{2\alpha}$. Both of these molecules are synthesized within the pregnant and non-pregnant uterus. While $PGE_2$ and $PGF_{2\alpha}$ are similar in mediating some effects, they are different with respect to certain others. Both cause uterine contractions, but they predominate at different sites within the uterus—$PGE_2$ in the lower uterine segment, $PGF_{2\alpha}$ in the fundal region. Both play important roles during labor, but $PGE_2$ has its major effect in cervical ripening, whereas $PGF_{2\alpha}$is more important in generating uterine contractions. $PGE_2$ elevates body temperature, whereas $PGF_{2\alpha}$has no apparent effect on body temperature. $PGE_2$ is vasodilator and bronchodilator, while $PGF_{2\alpha}$is a bronchoconstrictor and vasoconstrictor. See Catanzarite at 21–22.

Prostaglandins have been used in gynecology for pregnancy termination. Preparing the cervix with a prostaglandin suppository has been found to reduce the incidence of cervical laceration and significant bleeding. See Catanzarite at page 22. Synthetic analogues of prostaglandin $PGE_2$, such as 16-16-dimethyl $PGE_2$ and 9-methylene $PGE_2$, have proven useful for the induction of first trimester abortions. Such procedures typically use vaginal suppositories containing 20 milligrams $PGE_2$ or 3 milligrams of 15-methyl $PGF_{2\alpha}$, or by repeated intramyometrial injections of 15-methyl $PGF_{2\alpha}$, or by infusing a $PGF_{2\alpha}$-urea mixture (20 milligrams of $PGF_{2\alpha}$and 40 milligrams of urea in 100 mL of 5% dextrose in water) into the amniotic sac.

In obstetrics, prostaglandins have been used for cervical ripening, labor induction and control of post-partum hemorrhage. Catanzarite at 29. For cervical ripening, $PGE_2$ has been given intravenously, orally and vaginally, but the preferred route is intracervically. A $PGE_2$ gel is now commercially available in Scandinavia, and another $PGE_2$ gel is being investigated in the United States. The $PGE_2$ gel can also be used for labor induction (3–5 mg of $PGE_2$, prepared by blending a 20 mg suppository with 60 mL of lubricating jelly and using 9–15 mL of the mixture, is placed in the vagina). Catanzarite at 32. Prostaglandins have also been utilized to control post-partum hemorrhage.

Topical and transdermal drug formulations are designed to deliver a therapeutically effective amount of drug to or across the skin of a patient. Devices known to the art include reservoir type devices involving membranes that control the rate of drug release to the skin, gels and creams, and devices involving a dispersion of the drug in a matrix such as a pressure sensitive adhesive. As the skin presents a barrier to the drug it is often desirable or necessary to incorporate certain materials that enhance the rate at which the drug passes through the skin. For any particular drug, however, the type of device, the transdermal flux rate that is suitable, and suitable formulation components, are dependent upon the particular drug to be delivered.

Topical and transdermal administration of $PGE_1$ and $PGE_1$ derivatives have also been described, e.g., in U.S. Pat. Nos. 4,889,845 (Ritter et al.), 4,515,810 (Chow et al.), and 5,219,885 (Froelich et al.) and in Japanese Kokai 2-264725 (Morimoto et al.) and 63-135333 (Nakano et al.). In order for a transdermal formulation of $PGE_1$ or a derivative thereof to be effective and suitable it is desirable that the formulation have a high transdermal flux rate, allowing a therapeutically effective blood level of the drug to be achieved or maintained when the formulation is applied to a relatively small area of the skin. Furthermore $PGE_1$ readily undergoes certain reactions and rearrangements (see. e.g., J. Chromatography, 1991, 555, 73 (Lee et al.). This instability of the prostaglandin can be problematic in providing a suitable transdermal formulation.

SUMMARY OF THE INVENTION

The invention provides topical compositions and methods of treatment for female sexual dysfunction. The invention also provides methods for ameliorating female sexual dysfunction by modulating arousal and the excitation and plateau phases of the female sexual response on demand by topical application of an effective amount of prostaglandin $E_1$.

The composition of the invention is suitable for topical application, and comprises a vasoactive agent, preferably a prostaglandin, more preferably prostaglandin $E_1$, a polymer thickener, a lipophilic component, and an acidic buffer system. In several preferred embodiments, the polymer thickener is a polyacrylic acid polymer. In other preferred embodiments, the polymer thickener is a polysaccharide gum. The lipophilic component is chosen from the group consisting of the $C_1$ to $C_8$, aliphatic alcohols, the $C_2$ to $C_{30}$ aliphatic esters and mixtures thereof. The acidic buffer system is chosen to provide a suitable pH to minimize irritation of skin and mucous membranes. The composition is typically in the form of a cream, lotion, gel or other form suitable for topical application to skin and mucous membranes.

The prostaglandin is present in a formulation of the invention in a therapeutically effective amount. Therapeutic effectiveness can be assessed, in part, with increase in vaginal secretion, increase in vaginal engorgement, increase in sexual responsiveness and increase in arousal.

The present invention provides the use of compositions comprising prostaglandin $E_1$ for the manufacture of a medicament for topical or transdermal administration to modulate sexual response in a human female. While not being tied to a specific mechanism, it is believed that prostaglandin $E_1$ acts directly on local tissues to produce increases in vaginal secretion, increases in vaginal engorgement, and acts indirectly on the central nervous system to increase sexual responsiveness and arousal.

The methods of the present invention may be used to improve or enhance arousal and sexual response in women whose sexual response is impaired as evidenced by diminished capacity to produce sufficient vaginal lubrication to facilitate comfortable penile penetration and by other symptoms of impaired sexual responsiveness. The invention thus provides a method of ameliorating female sexual arousal disorder, comprising the step of administering to a human female a composition suitable for topical application comprising an effective amount of a prostaglandin, a polymer carrier, a lipophilic component, and a buffer system, typically in a cream, lotion, gel or other suitable form.

The effective amount of prostaglandin to be administered is selected to provide increased blood flow to the genitalia, which may be assessed by visual inspection, vaginal photoplethysmography, vaginal lubrication or engorgement. Alternatively, the effective amount to be administered is selected to provide increased sexual response, which may be assessed by visual inspection, vaginal photoplethysmography, vaginal lubrication and engorgement of the genitalia.

The effective amount of prostaglandin to be administered to increase arousal is selected to provide increased arousal as measured by self-report by a suitable questionnaire.

In the absence of any clinically diagnosed dysfunction in the female sexual response, the methods of the present invention may also be used to enhance the sexual response in a human female not suffering from a sexual dysfunction. The present invention will allow a more rapid response to sexual stimulation along with heightened sensation associated with excitement and plateau stages of the female sexual response by virtue of the increased blood flow to the tissues, as well as enhance subjective aspects, thereby leading to relatively increased arousal. The invention thus provides a method of enhancing female sexual arousal, comprising the step of administering to a human female a composition suitable for topical application comprising an effective amount of a prostaglandin, a polymer carrier, a lipophilic component, and a buffer system, typically in a cream, lotion, gel or other suitable form.

The invention further provides a method of enhancing female sexual response, comprising the step of administering to a human female a composition suitable for topical application comprising an effective amount of a prostaglandin, a polymer carrier, a lipophilic component, and a buffer system, typically in a cream, lotion, gel or other suitable form.

The invention also provides an article of manufacture comprising a container having a closure, a composition suitable for topical application comprising prostaglandin $E_1$ and a label that provides instructions for use in human females. Suitable containers include tubes, jars, vials and unit dosage forms. The closure may be recloseable, for example, a screw cap or a tight snap-fit cap.

DETAILED DESCRIPTION OF THE PREFERRED EMBODIMENTS

Figure 1:
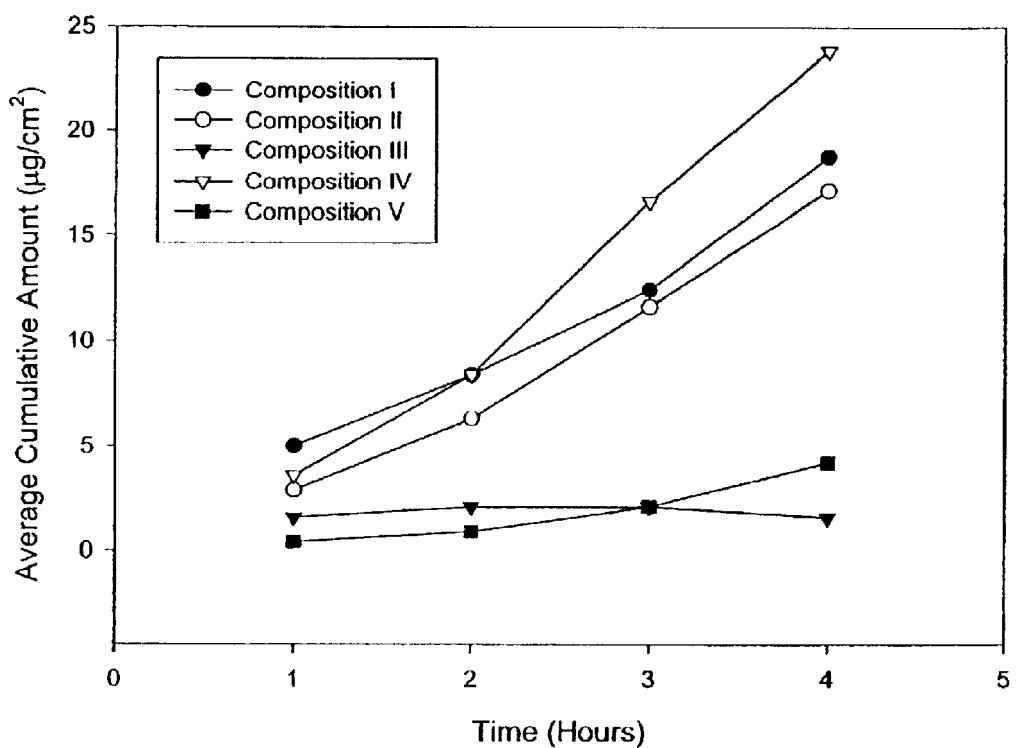
FIG. 1 is a graphical representation of the results of experiments in which the permeation of prostaglandin $E_1$ after application of different compositions to a model system, shed snake skin.

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "a vasoactive agent" includes a mixture of two or more such drugs, reference to "a penetration enhancer" includes mixtures of two or more enhancers, and the like.

In describing and claiming the present invention, the following terminology will be used in accordance with the definitions set out below.

The term "drug" or "pharmacologically active agent" as used herein is intended to mean a compound or composition of matter which, when administered to an organism (human or animal) induces a desired pharmacologic and/or physiologic effect by local and/or systemic action. As noted above, the pharmacologically active agents used in conjunction with the present invention are vasoactive agents.

By "transdermal" drug delivery, applicant is using the term in its conventional sense, i.e., to indicate delivery of a drug by passage into and through the skin and the underlying tissues and into the blood stream. By "transmucosal" drug delivery, applicant intends delivery of a drug by passage of a drug through the mucosal and underlying tissue into the blood stream. The compositions, systems, and methods of the invention, unless explicitly stated otherwise, should be presumed to be equally applicable to either transdermal or transmucosal modes of drug delivery.

"Penetration enhancement" or "permeation enhancement" as used herein relates to an increase in the permeability of the skin or mucosal tissue to a selected pharmacologically active agent, i.e., so that the rate at which the drug permeates through the skin or mucosal tissue is increased. "Carriers" or "vehicles" as used herein refer to carrier materials suitable for transdermal or transmucosal drug administration, and include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect.

In order to carry out the method of the invention, a composition suitable for topical application comprising a selected vasoactive agent is administered about fifteen minutes to about one hour prior to the time of desired effect. Preferably, the topical composition is applied once, twice or three times within a twenty-four hour period.

Suitable vasoactive agents include, but are not limited to: nitrates such as nitroglycerin, isosorbide dinitrate, erythrityl tetranitrate, amyl nitrate, sodium nitroprusside, molsidomine, linsidomine chlorhydrate and S-nitroso-N-acetyl-d,l-penicillamine ("SNAP"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; trazodone and vasoactive intestinal peptides. Prostaglandin $E_1$ and phentolamine are particularly preferred vasoactive agents for use in conjunction with the present method.

A dose of a prostaglandin $E_1$ in an amount sufficient to enhance engorgement or vaginal secretion is topically administered to a woman. The appropriate doses of the particular vasodilating agent may be readily determined using methods described in Examples 3 and 4, below. The female response may be measured using methods described in Masters, W. H. and Johnson, V. E., *Human Sexual Response*, Little, Brown, and Co., Boston (1966) which is incorporated herein by reference. Engorgement and redness of the external genitalia can be assessed by visual inspection. Methods for measuring blood flow, including Doppler ultrasonic velocimetry, thermography using for example an isothermal blood flow transducer, radioscintigraphic methods, vaginal photoplethysmography may be used as well as other methods well known in the art. In addition, measuring the contraction of the distal ⅓ as is characteristic of the plateau phase of female sexual response of the vagina may be measured using methods and equipment well known in the art including but not limited to strain gauges or other devices for measuring muscular contraction or muscle tension.

In addition, enhanced sexual response and heightened arousal can be measured using a questionnaire that requests that the female subject to describe any change in sensation brought about by administration of the prostaglandin composition by the methods of the present invention. In determining as suitable effective dose, appropriate placebo controls can be used to determine whether or not the observed effect is directly attributable to the administration of the prostaglandin composition. A suitable questionnaire for the measurement of enhanced sexual response and heightened arousal is provided below in Example 4.

A preferred embodiment of the present invention involves the topical administration of from at least 0.5 mg to about 6 mg of prostaglandin $E_1$ to a female from about 1 minute to about 1 hour prior to, and in preparation for, intercourse. In a more preferred embodiment of the present invention about 0.7 mg to about 6 mg of prostaglandin $E_1$ is administered topically to a female. In another preferred embodiment of the present invention, about 1.4 mg to about 6 mg of prostaglandin $E_1$ is administered topically to a female. In another preferred embodiment of the present invention, about 1 mg to about 3 mg of prostaglandin $E_1$ is administered topically to a female.

A preferred composition comprises about 0.07 weight percent to about 0.4 weight percent of prostaglandin $E_1$ and a pharmaceutically acceptable excipient to form a composition suitable for topical application.

More particularly, in a preferred embodiment, the composition suitable for topical application of the present invention comprises:
  a) about 0.07 percent by weight of the total composition to about 0.4 percent by weight of the total composition of prostaglandin $E_1$;
  b) about 0.5 to about 5 percent by weight of the total composition of a suitable polymer;
  c) about 70 to about 90 percent by weight of the total composition of a buffer;
  d) about 0.5 to about 15 percent by weight of the total composition of a lipophilic component;
  e) about 0.4 to about 5 percent by weight of the total composition of an emulsifier; and
  f) about 50 to about 90 percent by weight of the total composition of water.

In addition, the present invention is concerned with a method for treating an human female suffering from sexual dysfunction. The method comprises administering an effective amount of the above disclosed topical composition by applying the topical composition to the genital area of a human female. Preferably the topical composition is applied to the labia, clitoris and the vulvar region of the vagina.

The stable, uniform, composition suitable for topical application of the present invention preferably contains prostaglandin as a vasoactive agent. "Prostaglandin" as used herein includes $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$ as well as semi-synthetic or synthetic derivatives of natural prostaglandins, including carboprost tromethamine, dinoprost tromethamine, dinoprostone, lipoprost, gemeprost, metenoprost, sulprostone and tiaprost. Prostaglandin $E_1$ is a preferred prostaglandin. Prostaglandin is present in the composition in an amount of about 0.07 percent by weight of the total composition to about 1 percent by weight of the total composition. Preferably, prostaglandin $E_1$, is present in the composition in an amount of about 0.07 percent by weight of the total composition to about 0.4 percent by weight of the total composition.

The amount that constitutes a therapeutically effective amount varies according to the particular prostaglandin to be delivered, the indication to be treated, the surface area of the skin and mucous membrane over which the formulation is to be placed, and on the other components of the composition. Accordingly it is not practical to enumerate particular preferred amounts but such can be readily determined by those skilled in the art with due consideration of these factors. Generally, however, the prostaglandin is present in an amount of about 0.07 to about 1 percent, preferably about 0.1 to about 1 percent by weight based on the total weight of the composition. In one preferred embodiment, prostaglandin $E_1$ is present in an amount of about 0.07 to about 0.4 percent by weight based on the total weight of the composition. The prostaglandin can be dissolved or substantially uniformly dispersed in the topical composition. It is preferably soluble (and dissolved) in the topical composition.

The topical composition can contain one or more penetration enhancers. Among the preferred penetration enhancers for the present invention are ethanol, propylene glycol, glycerol, ethyl laurate, isopropyl palmitate, isopropyl myristate, laurocapram (Azone™), dioxolanes (described in U.S. Pat. No. 4,861,764), macrocyclic ketones, HP-101, oxazolidones and biodegradable penetration enhancers (described in U.S. Pat. Nos. 4,980,378 and 5,082,866 to Wong et al. and U.S. Pat. No. 6,118,020 to Büyüktimkin et al. such as alkyl-2-(N-substituted amino) alkanoates (e.g., dodecyl N,N-dimethylamino isoproprionate (DDAIP)), N-substituted amino alkanol alkanoates), acid addition salts and mixtures thereof. The penetration enhancer is present in an amount sufficient to enhance the penetration of the prostaglandin $E_1$. The specific amount varies necessarily according to the desired release rate and the specific form of prostaglandin $E_1$ used. Generally, the penetration enhancer is present in an amount ranging from about 0.5 weight percent to about 20 weight percent, based on the total weight of the composition. Preferably, the penetration enhancer is present in an amount ranging from about 1 weight percent to about 10 weight percent of the composition. More preferably, the penetration enhancer is present in an amount ranging from about 1 weight percent to about 5 weight percent of the composition.

In general, suitable penetration enhancers can be chosen from those listed above as well as sulfoxides, alcohols, fatty acids, fatty acid esters, polyols, amides, surfactants, terpenes, alkanones, organic acids and mixtures thereof. See generally Chattaraj, S. C. and Walker, R. B., Penetration Enhancer Classification, pp.5–20 in Maibach, H. I., and Smith, H. E., (eds.), *Percutaneous Penetration Enhancers*, CRC Press, Inc., Boca Raton, Fla. (1995) and Büyüktimkin, N., et al., Chemical Means of Transdermal Drug Permeation Enhancement, in Gosh, T. K., et al., (eds.) *Transdermal and Topical Drug Delivery Systems*, Interpharm Press, Inc., Buffalo Grove, Ill. (1997). Suitable sulfoxides include dimethylsulfoxide, decylmethylsulfoxide and mixtures thereof. Suitable alcohols include ethanol, propanol, butanol, pentanol, hexanol, octanol, nonanol, decanol, 2-butanol, 2-pentanol, benzyl alcohol, caprylic alcohol, decyl alcohol, lauryl alcohol, 2-lauryl alcohol, myristyl alcohol, cetyl alcohol, stearyl alcohol, oleyl alcohol, linolyl alcohol, linolenyl alcohol and mixtures thereof. Suitable fatty acids include valeric, heptanoic, pelargonic, caproic, capric, lauric, myristic, stearic, oleic, linoleic, linolenic, caprylic, isovaleric, neopentanoic, neoheptanoic, neononanoic, trimethyl hexanoic, neodecanoic and isostearic acids and mixtures thereof.

Suitable fatty acid esters include isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate, ethyl oleate, ethyl laurate and mixtures thereof. Suitable polyols include propylene glycol, polyethylene glycol, ethylene glycol, diethylene glycol, triethylene glycol, dipropylene glycol, glycerol, propanediol, sorbitol, dextrans, butanediol, pentanediol, hexanetriol and mixtures thereof.

Suitable amides include urea, dimethylacetamide, diethyltoluamide, dimethylformamide, dimethyloctamide, dimethyldecamide, 1-alkyl-4-imidazolin-2-one, pyrrolidone derivatives, cyclic amides, hexamethylenelauramide and its derivatives, diethanolamine, triethanolamine and mixtures thereof. Suitable pyrrolidone derivatives include 1-methyl-2-pyrrolidone, 2-pyrrolidone, 1 -lauryl-2-pyrrolidone, 1-methyl-4-carboxy-2-pyrrolidone, 1-hexyl-4-carboxy-2-pyrrolidone, 1-lauryl-4-carboxy -2-pyrrolidone, 1-decylthioethyl-2-pyrrolidone (HP-101), 1-methyl-4-methoxycarbonyl -2-pyrrolidone, 1-hexyl-4-methoxycarbonyl-2-pyrrolidone, 1-lauryl-4-methoxycarbonyl -2-pyrrolidone, N-cyclohexylpyrrolidone, N-dimethylaminopropylpyrrolidone, N-cocoalkypyrrolidone, N-tallowalkypyrrolidone, fatty acid esters of N-(2-hydroxymethyl)-2-pyrrolidone and mixtures thereof. Suitable cyclic amides include 1-dodecylazacycloheptane-2-one (laurocapram, Azone®), 1-geranylazacycloheptan-2-one, 1-famesylazacycloheptan-2-one, 1-geranylgeranylazacycloheptan-2-one, 1-(3,7-dimethyloctyl)azacycloheptan-2-one, 1-(3,7,11-trimethyloctyl)azacycloheptan-2-one, 1-geranylazacyclohexane-2-one, 1-geranylazacyclopentan-2,5-dione, 1-famesylazacyclopentan-2-one and mixtures thereof.

Suitable surfactants include anionic surfactants, cationic surfactants, nonionic surfactants, bile salts and lecithin. Suitable anionic surfactants include sodium laurate, sodium lauryl sulfate and mixtures thereof. Suitable cationic surfactants include cetyltrimethylammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride, and mixtures thereof. Suitable nonionic surfactants include α-hydro-ω-hydroxy-poly (oxyethylene)-poly(oxypropyl) poly(oxyethylene)block copolymers, polyoxyethylene ethers, polyoxyethylene sorbitan esters, polyethylene glycol esters of fatty alcohols and mixtures thereof. Suitable α-hydro-ω-hydroxy-poly (oxyethylene)-poly(oxypropyl) poly(oxyethylene)block copolymers include Poloxamers 231, 182, and 184 and mixtures thereof. Suitable polyoxyethylene ethers include 4-lauryl ether (BRIJ 30™), (BRIJ 93™), (BRIJ 96™), 20-oleyl ether (BRIJ 99™) and mixtures thereof. Suitable polyoxyethylene sorbitan esters include the monolaurate (TWEEN 20™, SPAN 20™) the monopalmitate (TWEEN 40™), the monostearate (TWEEN 60™), and the monooleate (TWEEN 80™) and mixtures thereof. Suitable polyethylene glycol esters of fatty acids include the 8-oxyethylene stearate ester (MYRJ 45™), (MYRJ 51™), the 40-oxyethylene stearate ester (MYRJ 52™) and mixtures thereof. Suitable bile salts include sodium cholate, sodium salts of laurocholic, glycolic and desoxycholic acids and mixtures thereof.

Suitable terpenes include D-limonene, α-pinene, β-enrene, α-terpineol, terpinen-4-ol, carvol, carvone, pulegone, piperitone, menthone, menthol, geraniol, cyclohexene oxide, limonene oxide, α-pinene oxide, cyclopentene oxide, 1,8-cineole, ylang ylang oil, anise oil, chenopodium oil, eucalyptus oil and mixtures thereof. Suitable alkanones include N-heptane, N-octane, N-nonane, N-decane, N-undecane, N-dodecane, N-tridecane, N-tetradecane, N-hexadecane and mixtures thereof. Suitable organic acids include citric acid, succinic acid, salicylic acid, salicylates (including the methyl, ethyl and propyl glycol derivatives), tartaric acid and mixtures thereof.

Polysaccharide gums can be used as a polymer thickener in the present composition. Suitable representative gums are those in the galactomannan gum category. A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1→4). Single membered α-D-mannopyranosyl units, linked (1→6) with the main chain, are present as side branches. Galactomannan gums include guar gum, which is the pulverized endosperm of the seed of either of two leguminous plants (*Cyamposis tetragonalobus* and *Cyamposis psoraloids*) and locust bean gum, which is found in the endosperm of the seeds of the carobtree (*Ceratonia siliqua*). Locust bean gum is preferred for the present invention. Other suitable representative gums include agar gum, carrageenan gum, ghatti gum, karaya gum, rhamsan gum, alginic acid derivatives, cellulose derivatives and xanthan gum. The composition of the present invention may contain a mixture of various gums, or mixture of gums and acidic polymers. Gums, and galactomannan gums in particular, are well-known materials. See for instance, *Industrial Gums: Polysaccharides & Their Derivatives*, Whistler R. L. and BeMiller J. N. (eds.), 3rd Ed. Academic Press (1992) and Davidson R. L., *Handbook of Water-Soluble Gums & Resins*, McGraw-Hill, Inc., N.Y. (1980). Most gums are commercially available in various forms, commonly a powder, and ready for use in foods and topical compositions. For example, locust bean gum in powdered form is available from TIC Gums Inc. (Belcamp, Md.). The polysaccharide gums are represent in the range from about 0.5 percent to about 5 percent, based on the total weight of the composition, with the preferred range being from 0.5 percent to 3 percent. Illustrative compositions are given in the Examples, below.

In other embodiments, the topical composition contains a polyacrylic acid polymer thickener instead of, or in combination with, a polysaccharide gum. A common variety of polyacrylic acid polymer is known generically as "carbomer." Carbomer is polyacrylic acid polymers lightly cross-linked with polyalkenyl polyether. It is commercially available from the B. F. Goodrich Company (Akron, Ohio) under the designation "CARBOPOL™." A particularly preferred variety of carbomer is that designated as "CARBOPOL 940™." Other polyacrylic acid polymers suitable for use in practicing this invention are those commercially available under the designations "Noveon AA-1™" (B. F. Goodrich Company), "Pemulen™" (B. F. Goodrich Company) and "POLYCARBOPHIL™" (A. H. Robbins, Richmond, Va.). Noveon AA-1™ is a preferred polyacrylic acid polymer. The Pemulen™ polymers are copolymers of $C_{10}$ to $C_{30}$ alkyl acrylates and one or more monomers of acrylic acid, methacrylic acid or one of their simple esters crosslinked with an allyl ether of sucrose or an allyl ether of pentaerythritol. The POLYCARBOPHIL™ polymer is a polyacrylic acid cross-linked with divinyl glycol. Where polyacrylic acid polymers are present, they represent about 0.5 percent to about 5 percent of the composition, based on its total weight.

Another important component of the present invention is a lipophilic component. The term lipophilic component as used herein refers to an agent, preferably a mixture of agents, that is both lipophilic and hydrophilic. The $C_1$ to $C_8$, aliphatic alcohols, the $C_2$ to $C_{30}$ aliphatic esters, and their mixtures can serve as lipophilic component. Illustrative suitable alcohols are ethanol, n-propanol and isopropanol, while suitable esters are ethyl acetate, butyl acetate, ethyl laurate, methyl propionate, isopropyl palmitate and isopropyl myristate. As used herein, the term "aliphatic alcohol" includes polyols such as glycerol, propylene glycol and polyethylene glycols. A mixture of alcohol and ester is preferred, and in particular, a mixture of ethanol and ethyl laurate is most preferred. The concentration of lipophilic component required necessarily varies according to other factors such as the desired semi-solid consistency and the desired skin penetration promoting effects. The preferred topical composition contains lipophilic compound in the range of 7 percent to 40 percent by weight based on the total weight of the composition. Where a lipophilic component that is a mixture of aliphatic alcohol and aliphatic ester is used, the preferred amount of alcohol is in the range of 5 percent to 15 percent, while that of aliphatic ester is in the range from 2 percent to 15 percent (again based on the total weight of the composition).

In one embodiment, the $C_2$ to $C_{30}$ aliphatic esters, and their mixtures comprising the lipophilic compound include $C_8$ to $C_{30}$ aliphatic esters of glycerol selected from the group consisting monoglycerides, diglycerides, triglycerides, and mixtures thereof. Suitable aliphatic esters include glyceryl esters of saturated fatty acids, unsaturated fatty acids and mixtures thereof. Suitable saturated fatty acids include caproic acid, caprylic acid, capric acid, lauric acid, myristic acid, palmitic acid, stearic acid, arachidic acid, behenic acid and lignoceric acid. Suitable unsaturated fatty acids include oleic acid, linoleic acid and linolenic acid. Suitable glyceryl esters include glyceryl monooleate, triolean, trimyristin and tristearin, perferably trimyristin.

The concentration of lipophilic compound required necessarily varies according to other factors such as the desired semi-solid consistency and the desired skin penetration promoting effects. Suitably the concentration of lipophilic compound is in the range of 0.5 percent to 40 percent by weight based on the total weight of the composition. The preferred topical composition contains lipophilic compound in the range of 7 percent to 40 percent by weight based on the total weight of the composition.

Where a mixture of aliphatic alcohol and aliphatic ester are employed, the suitable amount of alcohol is in the range of about 0.5 percent to 10 percent. In one preferred embodiment, the amount of alcohol is in the range of about 5 percent to 15 percent, while that of aliphatic ester is in the range of about 2 percent to 15 percent (again based on the total weight of the composition). In another preferred embodiment, the amount of alcohol is in the range of about 0.5 percent to 10 percent, while that of aliphatic ester is in the range of 0 percent to 10 percent (again based on the total weight of the composition).

An optional, but preferred, component of the present invention is an emulsifier. Although not a critical factor, preferable emulsifiers generally exhibit a hydrophilic-lipophilic balance (HLB) number of at least 9. Sucrose esters, and specifically sucrose stearate, can serve as emulsifiers for the topical composition of the present invention. Sucrose stearate is a well known emulsifier available from various commercial sources.

Typical non-ionic surfactants include the polysorbates, which are mixtures of partial esters of sorbitol and its mono- and dianhydrides, typically condensed with approximately 20 mol of ethylene oxide; polyethyoxylated alkyl ethers and esters, in which the alkyl chain can be either saturated, unsaturated, branched or linear; polyethoxylated alkyl phenols, in which the hydrophobic group normally octyl or nonylphenol; and poloxamers, polyoxyethylene-polyoxypropylene block copolymers, in which the polyoxypropylene chain acts as the hydrophobic moiety. Some commercially available non-ionic surfactants are BRIJ 99™, BRIJ 78™, polyoxyl 40 stearate and polysorbate 80. BRIJ 99™ and BRIJ 78™ are polyethylene glycol fatty alcohol ethers. Polyoxyl 40 stearate is a mixture of mono- and distearate esters of polyoxyethylene and of free polyoxyethylene. Polysorbate 80 is polyoxyethylene (20) sorbitan monooleate.

When an emulsifier is used, sucrose stearate present up to about 2 percent, based on the total weight of the composition, is preferred. The preferred amount of sucrose stearate emulsifier can also be expressed as a weight ratio of emulsifier to polysaccharide gum. A ratio of 1 to 6 emulsifier to gum is preferred generate the desired semi-solid consistency and separation resistance.

The present invention includes a buffer system. Buffer systems serve to maintain or buffer the pH of compositions within a desired range. The term "buffer system" or "buffer" as used herein has reference to a solute agent or agents which, when in a water solution, stabilize such solution against a major change in pH (or hydrogen ion concentration or activity) when acids or bases are added thereto. Solute agent or agents which are thus responsible for a resistance to change in pH from a starting buffered pH value in the range indicated above are well known. While there are numerous other suitable buffers, such as acetate buffers, potassium phosphate monohydrate has proven effective for compositions of the present invention.

The final pH value of the pharmaceutical composition of the present invention may vary within the physiologically compatible range. Necessarily, the final pH value is not irritating to human skin. Without violating this constraint, the pH may be selected to improve prostaglandin $E_1$, stability and to adjust consistency when required. With these factors accounted for, the preferred pH value is about 3.0 to 7.4. The most preferred pH range is from about 3.5 to about 6.0.

The remaining component of the composition is water, which is preferably purified. The composition contains water in the range of about 50 to about 90 percent, optionally including at least some of the water in the buffer, based on the total weight of the composition. The specific amount of water present is not critical, however, being adjustable to obtain the desired consistency and/or concentration of the other components.

Additionally, known transdermal penetration enhancers can also be added, if desired. Illustrative are dimethyl sulfoxide (DMSO), dimethyl acetamide (DMA), 2-pyrrolidone, N,N-diethyl-m-toluamide (DEET), 1-dodecylazacycloheptane-2-one (laurocapram, Azone®, a registered trademark of Nelson Research), N,N-dimethylformamide, N-methyl-2-pyrrolidone, calcium thioglycolate, oxazolidinones, alkyl-2-(N-substituted amino) alkanoates and their acid addition salts (e.g., dodecyl N,N-dimethylamino isoproprionate (DDAIP)), N-substituted amino alkanol alkanoates and their acid addition salts, dioxolane derivatives, laurocapram derivatives, macrocyclic enhancers such as macrocyclic ketones and mixtures thereof.

Stabilizers, coloring agents, rheological agents, fragrances and preservatives can be added to the extent that they do not overly limit prostaglandin $E_1$ skin penetration or prevent the desired semi-solid consistency. When present, such are usually added in amounts of about 0.05 to about 0.30%. Suitable preservatives include methylparabens (methyl PABA), propylparabens (propyl PABA) and butyl-hydroxy toluene (BHT). The compositions of the present invention can also include a small amount, about 0.01 to about 4% by weight, of a topical anesthetic, if desired. Typical anesthetics include lidocaine and dibucaine.

Contemplated dosage forms of the semi-solid pharmaceutical composition of the present invention are creams, gels, and the like, also including but not limited to compositions suitable for use with transdermal patches and like devices.

The semi-solid composition of the present invention has a suitably chosen viscosity such that the composition is naturally retained where applied. The semi-solid composition can exhibit Newtonian or non-Newtonian Theological characteristics. In some preferred embodiments, the semi-solid composition of the present invention exhibits non-Newtonian rheological characteristics, i.e. in which the apparent viscosity is dependent on the shear rate applied to the composition. Preferably the composition has "shear-thinning" rheological properties. As used herein, "shear-thinning" refers to a reduction in apparent viscosity (the ratio of shear stress to the shear rate) with increasing shear rate, whether the reduction in apparent viscosity is time independent (pseudoplastic), time dependent (thixotropic) or associated with a yield stress, defined as a stress that must be exceeded before flow starts, (Bingham plastics and generalized Bingham plastics). See, generally, Harris, J., & Wilkinson, W. L., "Non-newtonian Fluid," pp.856–858 in Parker, S. P., ed., McGraw-Hill Encyclopedia of Physics, Second Edition, McGraw-Hill, New York, 1993. Suitable viscosity ranges from about 5,000 centipoise (cps) to about 20,000 cps, preferably from about 7,000 cps to about 13,000 cps.

The topical composition is applied to the labia, clitoris and vagina and massaged until absorption is complete. Amounts of the topical composition ranging between about 0.1 and about 10 grams and preferably about 0.1 to about 3 grams are sufficient for vasodilation and the erectile process to occur. The present invention can be used with or without benefit of erotic stimuli. The determination of an ideal dose of the composition should be determined with each individual by one skilled in the art, such as a physician or sex therapist. The effective amount to be administered is selected to provide increased blood flow to the genitalia, which may be assessed by visual inspection, vaginal photoplethysmography, vaginal lubrication or engorgement. The preferred active component is prostaglandin, most preferably prostaglandin $E_1$. Suitable doses of these selected drugs and other suitable drugs, such as phentolamine, will be apparent to those skilled in the art, or may be deduced from the literature in combination with the teaching of the present disclosure.

While this invention has been described by way of preferred embodiments, the examples set out herein are not intended to limit the scope of the invention which contemplates the use of any pharmacologic vasodilating drug capable of absorption into the local and systemic circulation upon administration of the drug via the transmucosal, transdermal, intranasal, buccal or rectal routes of administration.

Numerous other advantages of the present invention will be apparent from the following detailed description of the invention including the accompanying examples and the appended claims.

EXAMPLE 1

Formulation of Suitable Compositions

Composition I was prepared as follows according to Formulation I (Table 1, below). Part A was formed by dissolving about 0.4 parts prostaglandin $E_1$ (Alprostadil USP) in about 5 parts ethyl alcohol. Next, about 5 parts ethyl laurate were mixed into the alcohol-prostaglandin $E_1$ solution. Part B was prepared starting from a pH 5.5 water/buffer solution. The water/buffer solution was prepared by adding sufficient potassium phosphate monobasic to purified water to create a 0.1 M solution. The water/buffer solution diluted to a final concentration of about 0.05 M and about pH 5.5, adjusted with a strong base solution (1 N sodium hydroxide) and a strong acid (1 N phosphoric acid). Suitable buffer concentrations range from about 0.005 M to about 1.0 M. Preferred buffer concentrations range from about 0.05 M to about 0.2 M. In several preferred embodiments the buffer concentration is 0.1 M. Propylene glycol (about 5 parts) was added to the water/buffer solution, and then the polyacrylic polymer (about 1 part) was dispersed in the propylene glycol/water/buffer solution. All parts specified herein are parts by weight.

Parts A and B were mixed and homogenized using a homogenizer. Table 1, below, contains a list of ingredients and proportions. The resulting composition was a spreadable, semi-solid suitable for application to the skin and mucous membranes without the need for supporting devices such as patches and adhesive strips. The composition was both homogenous in appearance and resistant to separation. Compositions based on formulations II–VII were prepared following the same procedure.

TABLE 1

| Component | Formulation | | | | | | |
|---|---|---|---|---|---|---|---|
| | I (weight %) | II | III | IV | V | VI | VII |
| Noveon AA-1 | 1 | 1 | 1 | 1 | | | |
| Ethanol | 5 | 5 | | 5 | 5 | 5 | 5 |
| Propylene glycol | 5 | 5 | 5 | | | | |
| Ethyl laurate | 5 | 5 | | 5 | 5 | 3 | 3 |
| 70% Sorbitol | | 5 | | | | | |

TABLE 1-continued

| Component | Formulation | | | | | | |
|---|---|---|---|---|---|---|---|
| | I (weight %) | II | III | IV | V | VI | VII |
| Glycerol | | | 5 | | | | |
| DDAIP | | | | 5 | | 2.5 | |
| DDAIP HCl | | | | | | | 2.5 |
| Sesame oil | | | 5 | | | | |
| Squalene | | | 5 | | | | |
| Prehydrated Locust bean gum | | | | | 3 | | |
| Modified Guar Gum | | | | | | 3 | 2.5 |
| Sucrose stearate | | | | | 0.5 | | |
| 0.05M pH 5.5 buffer | 78.85 | 73.85 | 73.85 | 78.85 | 86.1 | 81 | |
| 0.1M pH 5.5 buffer | | | | | | | 87 |
| 1M NaOH | 4.75 | 4.75 | 4.75 | 4.75 | | | |
| Prostaglandin $E_1$ | 0.4 | 0.4 | 0.4 | 0.4 | 0.4 | 0.3 | 0.3 |

As noted above, in other embodiments, such as Compositions VI and VII, the composition may include a modified polysaccharide gum, suitably a modified galactomannan gum, such as a guar gum. Alternatively, a polyacrylic polymer may be used instead of the polysaccharide gum.

EXAMPLE 2

In Vitro Penetration Of Different Formulations

The relative ability of compositions prepared according to the formulations of Table 1 to provide prostaglandin $E_1$ was studied in two in vitro model systems corresponding to skin and mucosal membranes: shed snake skin and sheep vaginal membrane. The results are presented in FIGS. 1–3.

Compositions were evaluated for skin penetration using shed snake skin as a model barrier. Shed snake skin was obtained from the Animal Care Unit of the University of Kansas. With head and tail sections removed, the skin was randomly divided into test sections and then hydrated by soaking.

Samples of the compositions listed in Table 1 were evaluated using modified Franz-type diffusion cells (surface area 1.8 cm$^2$). Specifically, skin pieces were mounted on top of a receptor cell of a vertical diffusion cell assembly in which a small magnetic bar was inserted and filled with an isotonic buffer. A seal was placed on top of the skin section followed by a donor cell. The two cells were then clamped together. Known amounts of the formulations were applied on the bottom of a small capped vial (weight about 5 grams) which fits exactly to the donor cell to ensure uniform distribution. The vials were placed on the skin in the donor cell. To reduce the evaporation of the ingredients, the donor cell and vial were gently taped together with a water-resistant adhesive band. The cells were transferred to a stirred water bath that was maintained at 37 degrees Celsius. Samples were withdrawn from the cells each hour for four hours and analyzed for the concentration of prostaglandin $E_1$, with changes in concentration indicating the amount penetrating. Tests with multiple skin samples from the same snake yielded data that were averaged.

For a discussion of the use of shed snake skin in the evaluation of drug penetration, see U.S. Pat. No. 4,771,004 to Higuchi, which is incorporated here by reference to the extent that it is not inconsistent.

The results of the penetration study are presented in FIG. 1 and in Table 2, below. Prostaglandin $E_1$ penetrated quickly at a relatively sustained rate for four hours from compositions prepared based on Formulations I, II and III. In contrast, relatively little penetration was observed using compositions based on Formulations IV and V.

TABLE 2

Prostaglandin $E_1$ Average Cumulative Amount ($\mu g/cm^2$)

| Hour | Formulation I | Formulation II | Formulation III | Formulation IV | Formulation V |
|---|---|---|---|---|---|
| 1 | 5.00 | 2.89 | 1.58 | 3.55 | 0.39 |
| 2 | 8.42 | 6.32 | 2.11 | 8.42 | 0.92 |
| 3 | 12.37 | 11.58 | 2.11 | 16.58 | 2.11 |
| 4 | 18.68 | 17.11 | 1.58 | 23.82 | 4.21 |

EXAMPLE 3

Concentration Effects On In Vitro Penetration

The effect of the prostaglandin E1 concentration on permeation was studied using stripped shed snake skin. Stripped shed snake skin was prepared by removing the outer scale layer of the shed snake skin by 3–5 cycles of application and removal of adhesive tape (Minnesota Mining and Manufacturing Co., St. Paul, Minn.). The compositions tested were prepared as described in Example 1, and had final proportions (parts) of prostaglandin $E_1$, (either 0.05%, 0.1%, or 0.2%); ethanol, about 5 parts; propylene glycol, about 5 parts; ethyl laurate, about 5 parts; polyacrylic polymer, about 1 part; 1 M NaOH about 4.75 parts; 0.005 M phosphate buffer, about pH 5.5, q.s. 100.

Figure 2:
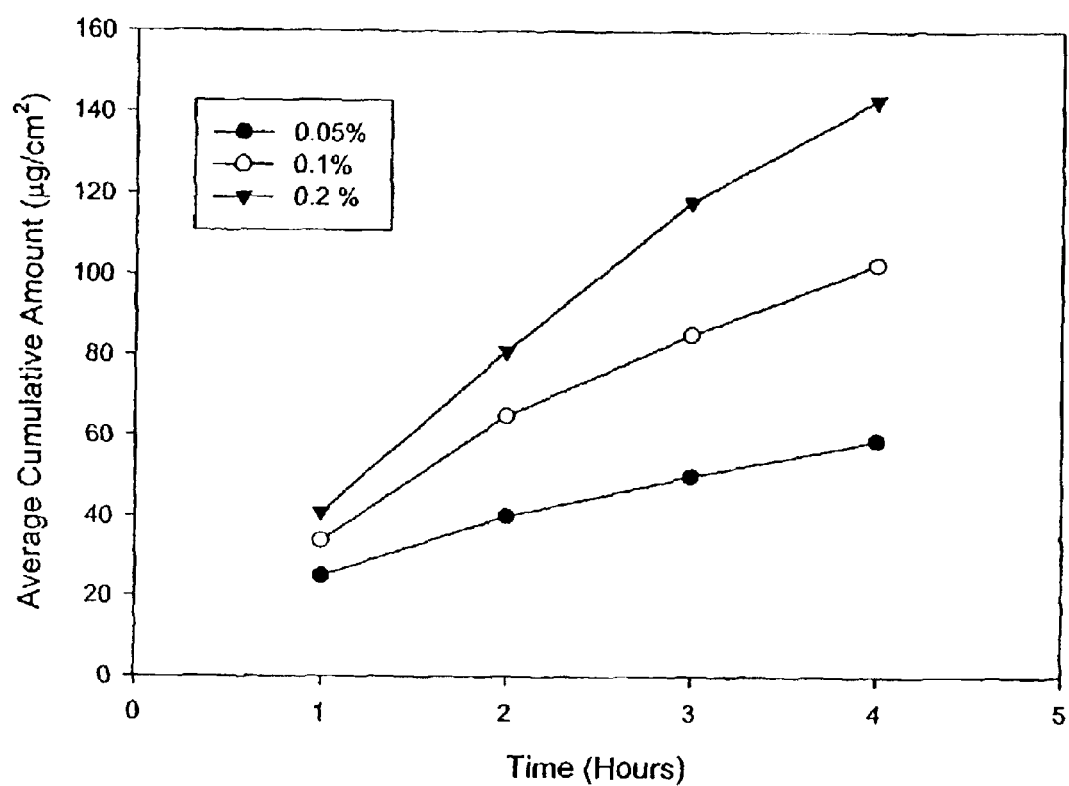
FIG. 2 is a graphical representation of the results of experiments in which the permeation of prostaglandin $E_1$ after application of compositions comprising different concentrations of prostaglandin $E_1$ to a model system, stripped shed snake skin.

Penetration studies were performed as described in Example 2. The results are shown in FIG. 2 and Table 3, below. Higher prostaglandin $E_1$ concentrations produce both more rapid permeation and a higher amount delivered.

TABLE 3

Prostaglandin $E_1$ Cumulative Amount ($\mu g/cm^2$)

| Hour | 0.05% Prostaglandin $E_1$ (Open Squares) | 0.1% Prostaglandin $E_1$ (Filled Triangles) | 0.2% Prostaglandin $E_1$ (Filled Squares) |
|---|---|---|---|
| 1 | 25 | 33.75 | 41 |
| 2 | 40 | 65 | 81 |
| 3 | 50 | 85 | 118 |
| 4 | 58.75 | 102.5 | 143 |

EXAMPLE 4

Comparison of Permeation in Two Model Membrane Systems

The permeation of prostaglandin $E_1$ in a topical composition of the present invention was compared using the stripped shed snake skin of Example 3 and the sheep vaginal membrane in vitro system. The topical composition used was the 0.2% prostaglandin $E_1$ composition of Example 3.

Sheep vaginas were obtained from a local slaughterhouse. The freshly excised organ was refrigerated and used immediately. After excision, the outer wall of the vagina was carefully separated from any adhering tissue, taking care to avoid damage. The vagina was cut open longitudinally (vertically) (Kabadi, M. B., and Chien, Y. W., Intravaginal controlled administration of Flurogestone acetate. II: Development of an in vitro system for studying the intravaginal release and permeation of Flurogestone acetate, *J. Pharm. Sci.* 73: 1464–1468 (1984)). The vaginal mucosa were separated from the interior of the vaginal wall, soaked in nanopure water, cut into appropriately sized pieces, and mounted in using modified Franz-type diffusion cells as described in Example 2.

Figure 3:
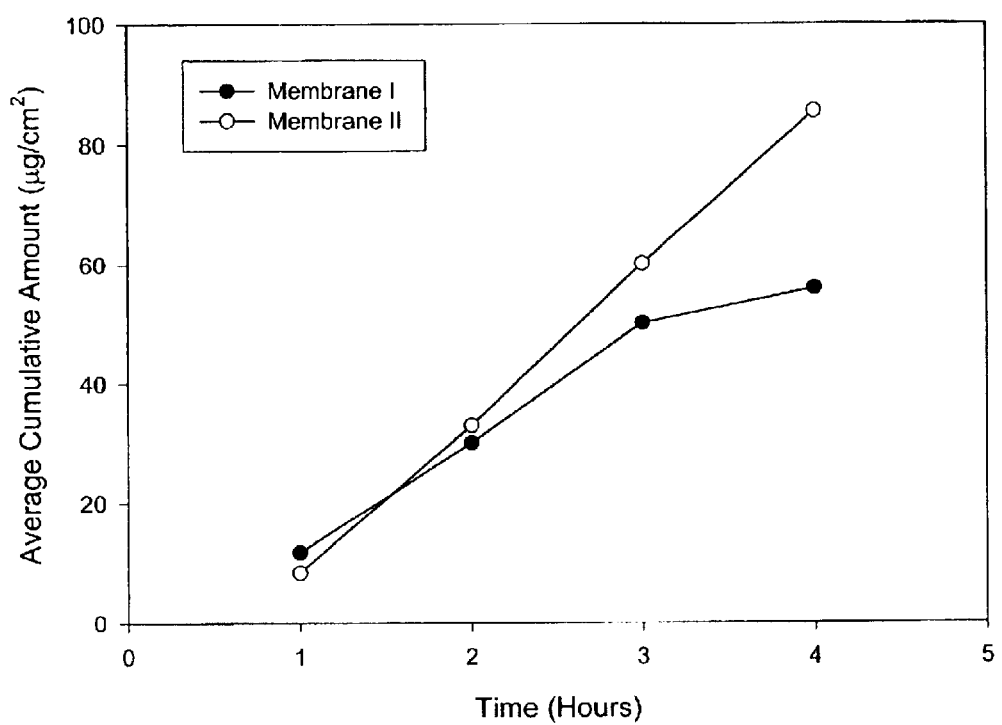
FIG. 3 is a graphical representation of the results of experiments in which the permeation of prostaglandin $E_1$ is compared in two model systems, stripped shed snake skin and sheep vaginal membrane.

Penetration studies were performed as described in Example 2. The results are shown in FIG. 3 and Table 4, below. The penetration measured in stripped shed snake is comparable to that measured in sheep vaginal membrane over the first two hours, diverging slightly at three hours.

TABLE 4

Prostaglandin $E_1$ Average Cumulative Amount ($\mu g/cm^2$)

| Hour | Stripped Shed Snake Skin (Membrane I) | Sheep Vaginal Membrane (Membrane II) |
|---|---|---|
| 1 | 11.67 | 8.33 |
| 2 | 30.00 | 32.92 |
| 3 | 50.00 | 60.00 |
| 4 | 55.83 | 85.42 |

EXAMPLE 5

Clinical Study in Women Suffering from Sexual Dysfunction

This study was conducted to evaluate the efficacy and safety of placebo and 3 doses of topical prostaglandin $E_1$ cream (compositions based on Formulation I of Example 1 containing either 0.05%, 0.1% or 0.2% prostaglandin $E_1$) in female subjects with FSAD in a controlled laboratory setting. Efficacy was assessed by vaginal photoplethysmography (Geer Gauge) during visual sexual stimulation (VSS), and by the use of quantitative patient questionnaires and diaries. Premenopausal subjects were enrolled under the assumption that their inherent magnitude of physiologic response is greater than that of postmenopausal subjects and thus will improve the likelihood of measuring pharmacologic effects. The study assessed the safety of 3 doses of topical prostaglandin $E_1$ cream in women with sexual dysfunction. The study also assessed the efficacy of 3 doses of topical prostaglandin $E_1$ cream in affecting vaginal blood flow and exudates and refinement of a quality of life instrument.

The study was a single center, single-blind, escalating dose, placebo-controlled pilot study to investigate the physiologic action, and the efficacy and safety of 3 doses of topical prostaglandin $E_1$ cream in women with FSAD. A total of 8 subjects were enrolled in this study. The study measured the dose-response characteristics of the safety and efficacy of the prostaglandin $E_1$ cream in terms of physiological response as well as the subjects' signs and symptoms and perceptions of the physiologic responses.

After signing the informed consent, at screening (Visit 1), the subjects underwent an adaptation session in the sexual response assessment laboratory. This session was intended to allow the patient to become familiar and comfortable with the procedures that will be carried out at subsequent visits. A complete medical history (including the Sexual Activity Questionnaire and the Brief Index of Sexual Function for Women (BISF-W; Taylor, J. F., et al., Self-report assessment of female sexual function: psychometric evaluation of the Brief Index of Sexual Functioning for Women. Arch Sexual Behavior: 23: 627–643, 1994.)) were collected. All medications taken by the patient were be recorded. Baseline safety assessments included ECG, physical exam (including pelvic exam), clinical laboratory tests, and vital signs. Subjects who met all inclusion and no exclusion criteria continued in the study.

The inclusion criteria for the study were that the female subjects aged 21 and provided written, informed consent; had a history of female sexual dysfunction (defined as impairment of the woman's ability to experience vaginal lubrication or engorgement sufficient for intercourse on at least 50% of attempts) of at least 6 months duration; were premenopausal; used adequate contraception (oral hormonal contraceptives, hormonal implants, or tubal ligation); had regular menses (cycles consistent in duration ±2 days and between 25 and 31 days in length; and had a normal Pap smear within the past year. Any patient with an ASCUS Pap, except, "ASCUS, favor dysplasia" was admitted. Any Pap smear with inflammation or inflammatory changes in the absence of clinically significant vaginitis was admitted.

Subjects with any of the following conditions or meeting any of the following criteria were excluded from the study: female sexual dysfunction caused by untreated endocrine disease, e.g., hypopituitarism, hypothyroidism, diabetes mellitus; positive serum beta HCG or UPT result; a history of chronic or complicated urinary tract or vaginal infections within previous 12 months; a history of pelvic inflammatory disease within previous 12 months; history of dyspareunia not attributable to vaginal dryness within previous 12 months; significant (moderate to severe) vaginal atrophy; presence of moderate to severe vaginitis on pelvic examination; cervical dysplasia; significant cervicitis as manifested by mucopurulent discharge from the cervix; evidence of clinically significant hepatic disease as evidenced by SGOT or SGPT>3 times the upper limit of normal within the last 6 months; evidence of clinically significant renal disease as evidenced by a serum creatinine>2.5 mg % within the last 6 months; a history of myocardial infarction within previous 12 months; symptomatic coronary artery disease, i.e., angina pectoris; symptomatic hypotension requiring medical consultation within the last 6 months; psychoses, uncontrolled bipolar disorder, uncontrolled depression; acute or chronic disease requiring frequent changes (changes within previous two months or anticipated in following two months) in medications or doses of chronic therapy; significant central nervous system diseases within the last 6 months i.e., stroke, spinal cord injury, etc.; participation in another study with an investigational drug or device during the 30 days prior to study entry, or planned during the study; any condition which would interfere with the patient's ability to provide informed consent, to comply with study instructions, or which might confound the interpretation of the study results; or any condition which would endanger the participant if she participated in this trial.

At Visit 2, subjects received a single-blinded intravaginal dose of placebo. The patient underwent visual sexual stimulation in the sexual response assessment laboratory. The Geer Gauge (vaginal photoplethysmograph) was applied according to the manufacturer's instructions and vaginal photoplethysmography was recorded continuously from 15 minutes prior to dosing until the end of the visual sexual stimulation, approximately 60 minutes postdose. Safety was assessed from vital sign measurements and by monitoring the occurrence of adverse events. The patient's external genitalia, the vagina, and the cervix were inspected. Questionnaires were administered.

At Visit 3, subjects received a single-blinded dose of prostaglandin $E_1$ cream (containing 0.5 mg $PGE_1$) applied to the labia, clitoris and the vulvar region of the vagina. All procedures from Visit 2 were repeated. If the patient tolerated this dose, she continued to the next visit. If the patient did not tolerate the dose in the clinic, she would dismissed from the study but receive appropriate follow-up medical care.

At Visit 4, subjects returned to the clinic and received a single-blinded dose of prostaglandin $E_1$ cream (containing 1.0 mg $PGE_1$) applied to the labia, clitoris and the vulvar region of the vagina. All procedures from Visit 2 were repeated. As before, if the patient tolerated this dose, she continued to the next visit. If the patient did not tolerate the dose in the clinic, she would dismissed from the study but receive appropriate follow-up medical care.

At Visit 5, subjects returned to the clinic and received a single-blinded dose of prostaglandin $E_1$ cream (containing 2.0 mg $PGE_1$) applied to the labia, clitoris and the vulvar region of the vagina. All procedures from Visit 2 were repeated. As before, if the patient tolerated this dose, she continued to the next visit. If the patient did not tolerate the dose in the clinic, she would dismissed from the study but receive appropriate follow-up medical care.

The eight subjects had an average age of 40.4±7.7 years, an average weight of 150.3±42.3 pounds, and an average height of 63.9±2.5 inches. There were six Caucasian, one black and one Asian. All 8 subjects completed the study. The results are presented in Tables 4–14 and FIGS. 4–10.

Figure 4:
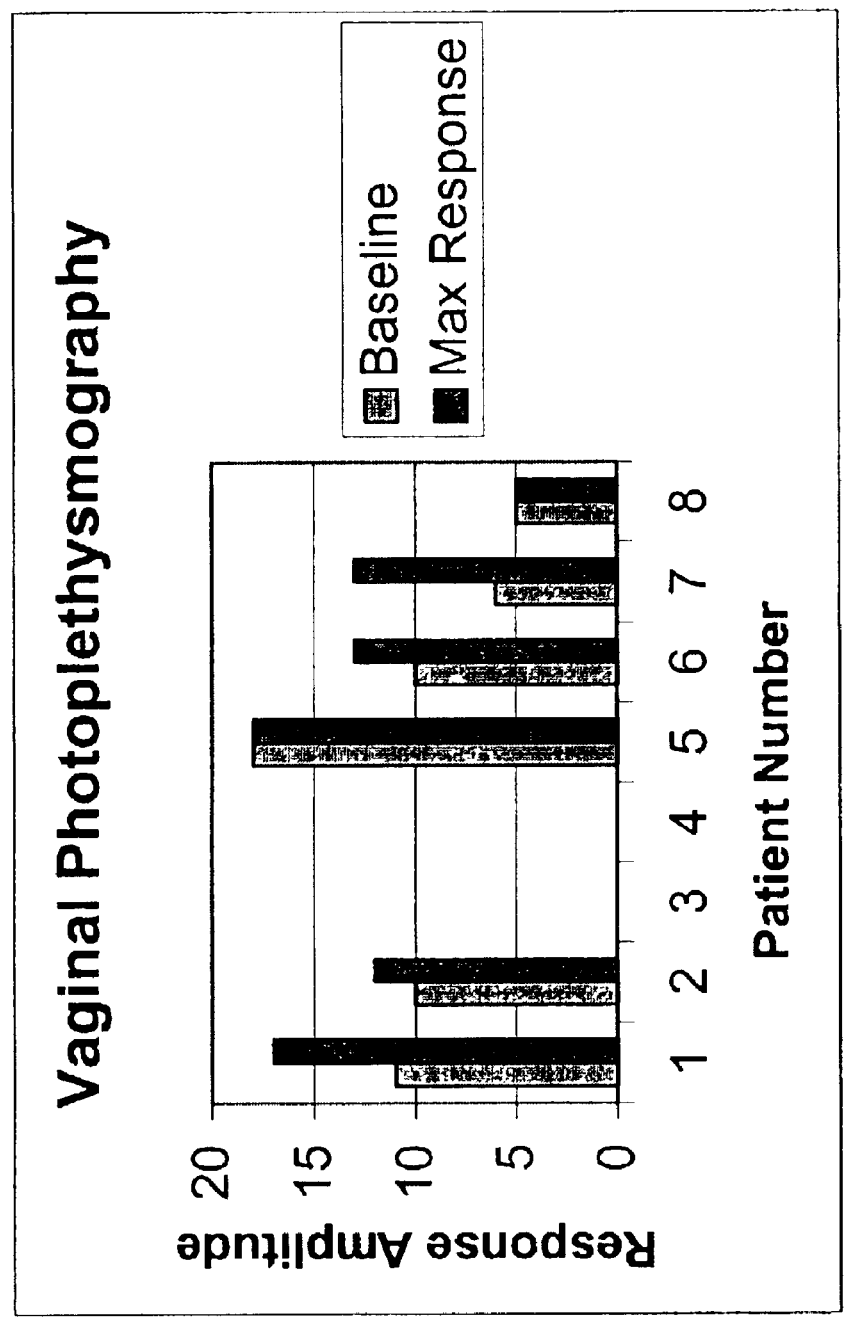
FIG. 4 is a graphical representation of the baseline responses and the maximum treatment responses of vaginal blood flow.
Figure 5:
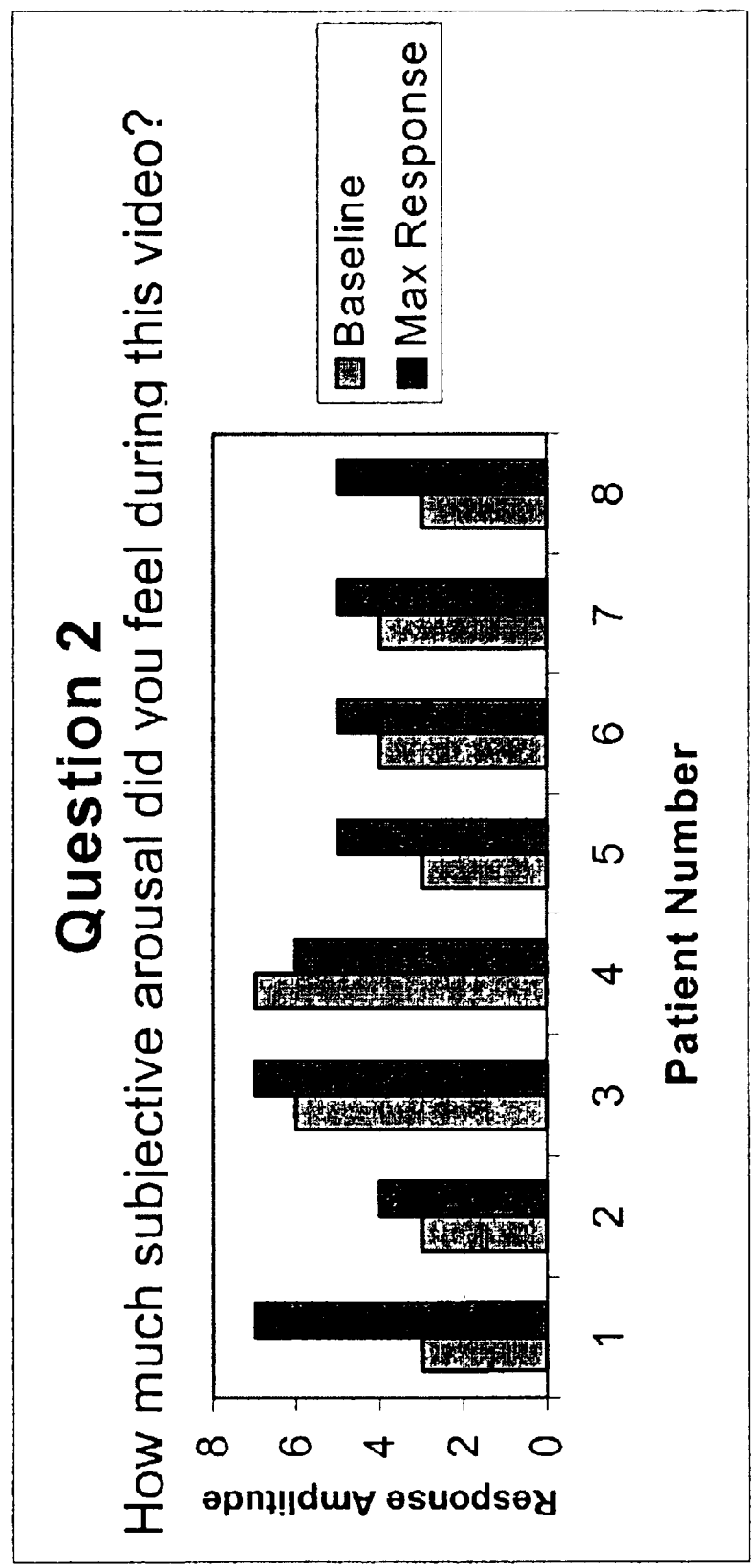
FIG. 5 is a graphical representation of the baseline responses and the maximum treatment responses to question 2 of the video assessment questionnaire.

Vaginal blood flow measurement, as maximum amplitude change in photoplethysmography measurements, did not show a statistically significant increase (FIG. 4, Table 5). However, there were no decreases seen on treatment. The lack of statistical significance may be related to the high baseline levels.

TABLE 5

VAGINAL BLOOD FLOW MEASUREMENT MAXIMUM AMPLITUDE CHANGE IN PHOTOPLETHYSMOGRAPHY MEASUREMENT
Means for Placebo, Treatment, and Within-Subject Change from Placebo

|  | PLACEBO (Visit 2) N = 6 | $PGE_1$ 0.05% (Visit 3) N = 8 | $PGE_1$ 0.1% (Visit 4) N = 8 | $PGE_1$ 0.2% (Visit 5) N = 7 |
|---|---|---|---|---|
| Mean at Visit | 10.00 ± 4.6* | 8.50 ± 4.1 | 10.88 ± 4.6 | 5.57 ± 3.5 |
| Change from Placebo |  | −1.50 ± 2.4** (p = 0.56) | 0.50 ± 1.6 (p = 0.77) | −1.50 ± 2.4 (p = 0.56) |

*Standard deviation
**Standard error

Video Assessment Questionnaire
Please answer the following questions in regard to the
erotic video that you have just seen. For Questions #2–4,
circle the number that best describes your response on a scale
from 0 to 10, with 0 meaning "not at
all" and 10 meaning "very much."

1. Which of the videos did you find most arousing?
   A     B     C     D
2. How much subjective arousal did you have during this video?
   Not at All                                              Very Much
   0     1     2     3     4     5     6     7     8     9     10
3. How much lubrication (wetness) did you feel during this video?
   Not at All                                              Very Much
   0     1     2     3     4     5     6     7     8     9     10
4. How much engorgement (fullness) did you feel during this video?
   Not at All                                              Very Much
   0     1     2     3     4     5     6     7     8     9     10
5. How much tingling did you feel in your vagina during this video?
   Not at All                                              Very Much
   0     1     2     3     4     5     6     7     8     9     10
6. How pleasurable were the feelings you had during the presentation of the video?
   Not at All                                              Very Much
   0     1     2     3     4     5     6     7     8     9     10
7. Did you notice any other physical sensations during presentation of the video?
   No     ☐
   Yes    ☐     Please describe those sensations:

8. Please rate the sensations described above in Question 7.
   I did not describe any sensations in Question 7.     ☐
   The sensations described in Question 7 were:
   Very Uncomfortable                                   Very Pleasurable
   0     1     2     3     4     5     6     7     8     9     10
9. How relaxed did you feel during the video presentation?
   Not at All                                              Very Much
   0     1     2     3     4     5     6     7     8     9     10
10. Did you have any problems/difficulties in watching the videos? Please specify:

The visual inspection by the investigator revealed several significant increases in objective measures related to the treatment with the topical composition with some analyses (Table 6), in particular an increase in erythema at all dosage levels and increases in exudates at the two higher dosages at each visit. In other analyses (Tables 7, 8), the changes seen did not reach the p=0.05 criterion of significance, with the exception of the exudate observations using 0.05% $PGE_1$ as reference.

TABLE 6

VISUAL INSPECTION
Pre-Treatment and Post-Treatment Means at Each Visit

|  | PLACEBO (Visit 2) N = 8 | $PGE_1$ 0.05% (Visit 3) N = 8 | $PGE_1$ 0.1% (Visit 4) N = 8 | $PGE_1$ 0.2% (Visit 5) N = 7 |
|---|---|---|---|---|
| ERYTHEMA |  |  |  |  |
| Pre | 1.00 ± 0** | 1.00 ± 0 | 1.13 ± .35 | 1.00 ± 0 |
| Post | 1.25 ± .46 | 1.63 ± .52 | 2.13 ± .83 | 2.29 ± .76 |
| Pre-Post* | p = 0.17 | p = 0.01 | p = 0.02 | p = 0.004 |
| SWELLING |  |  |  |  |
| Pre | 1.00 ± 0 | 1.00 ± 0 | 1.00 ± 0 | 1.00 ± 0 |
| Post | 1.13 ± .35 | 1.50 ± .53 | 1.25 ± .46 | 1.29 ± .49 |
| Pre-Post | p = 0.35 | p = 0.03 | p = 0.17 | p = 0.17 |

TABLE 6-continued

VISUAL INSPECTION
Pre-Treatment and Post-Treatment Means at Each Visit

|  | PLACEBO (Visit 2) N = 8 | $PGE_1$ 0.05% (Visit 3) N = 8 | $PGE_1$ 0.1% (Visit 4) N = 8 | $PGE_1$ 0.2% (Visit 5) N = 7 |
|---|---|---|---|---|
| EXUDATES |  |  |  |  |
| Pre | 1.38 ± 0.52 | 1.88 ± .64 | 1.63 ± .52 | 1.50 ± .53 |
| Post | 2.00 ± 0.76 | 2.25 ± .46 | 2.63 ± .52 | 2.57 ± .98 |
| Pre-Post | p = 0.05 | p = 0.08 | p = 0.001 | p = 0.005 |

*Change from pre-treatment to post-treatment, p-values based on paired t-tests.
**Standard deviation

TABLE 7

VISUAL INSPECTION
Comparisons of Mean Change From Pre- to Post-Treatment
Within Subjects, Using Placebo as the Reference

|  | PLACEBO (Visit 2) N = 8 | $PGE_1$ 0.05% (Visit 3) N = 8 | $PGE_1$ 0.1% (Visit 4) N = 8 | $PGE_1$ 0.2% (Visit 5) N = 7 |
|---|---|---|---|---|
| ERYTHEMA* | 0.25 ± .16*** | 0.63 ± .18 | 1.00 ± .33 | 1.29 ± .29 |
| Change** |  | 0.38 ± .26 (p = 0.20) | 0.75 ± .37 (p = 0.08) | 1.00 ± .31 (p = 0.018) |

TABLE 7-continued

VISUAL INSPECTION
Comparisons of Mean Change From Pre- to Post-Treatment Within Subjects, Using Placebo as the Reference

|  | PLACEBO (Visit 2) N = 8 | $PGE_1$ 0.05% (Visit 3) N = 8 | $PGE_1$ 0.1% (Visit 4) N = 8 | $PGE_1$ 0.2% (Visit 5) N = 7 |
|---|---|---|---|---|
| SWELLING | 0.13 ± .13 | 0.50 ± .19 | 0.25 ± .16 | 0.29 ± .18 |
| Change |  | 0.38 ± .26 (p = 0.20) | 0.13 ± .23 (0.60) | 0.14 ± .26 (0.60) |
| EXUDATES | 0.63 ± .26 | 0.38 ± .18 | 1.00 ± .19 | 1.14 ± .26 |
| Change |  | −0.25 ± .31 (p = 0.45) | 0.38 ± .26 (p = 0.20) | 0.57 ± .43 (0.23) |

*Mean of the difference between pre-treatment and post-treatment, using paired t-tests.
**Mean of the pre- to post-treatment change at each active drug visit, correcting for the change during treatment with placebo.
***Standard error

TABLE 8

VISUAL INSPECTION
Comparisons of Mean Change From Pre- to Post-Treatment Within Subjects, Using $PGE_1$ 0.05% as the Reference

|  | $PGE_1$ 0.05% (Visit 3) N = 8 | $PGE_1$ 0.1% (Visit 4) N = 8 | $PGE_1$ 0.2% (Visit 5) N = 7 |
|---|---|---|---|
| ERYTHEMA* | 0.63 ± .18*** | 1.00 ± .33 | 1.29 ± .29 |
| Change** |  | 0.38 ± .32 (p = 0.28) | 0.71 ± .29 (p = 0.047) |
| SWELLING | 0.50 ± .19 | 0.25 ± .16 | 0.29 ± .18 |
| Change |  | −0.25 ± .25 (p = 0.35) | −0.14 ± .14 (p = 0.36) |
| EXUDATES | 0.38 ± .18 | 1.00 ± .19 | 1.14 ± .26 |
| Change |  | 0.63 ± .18 (p = 0.011) | 0.71 ± .29 (p = 0.047) |

Figure 6:
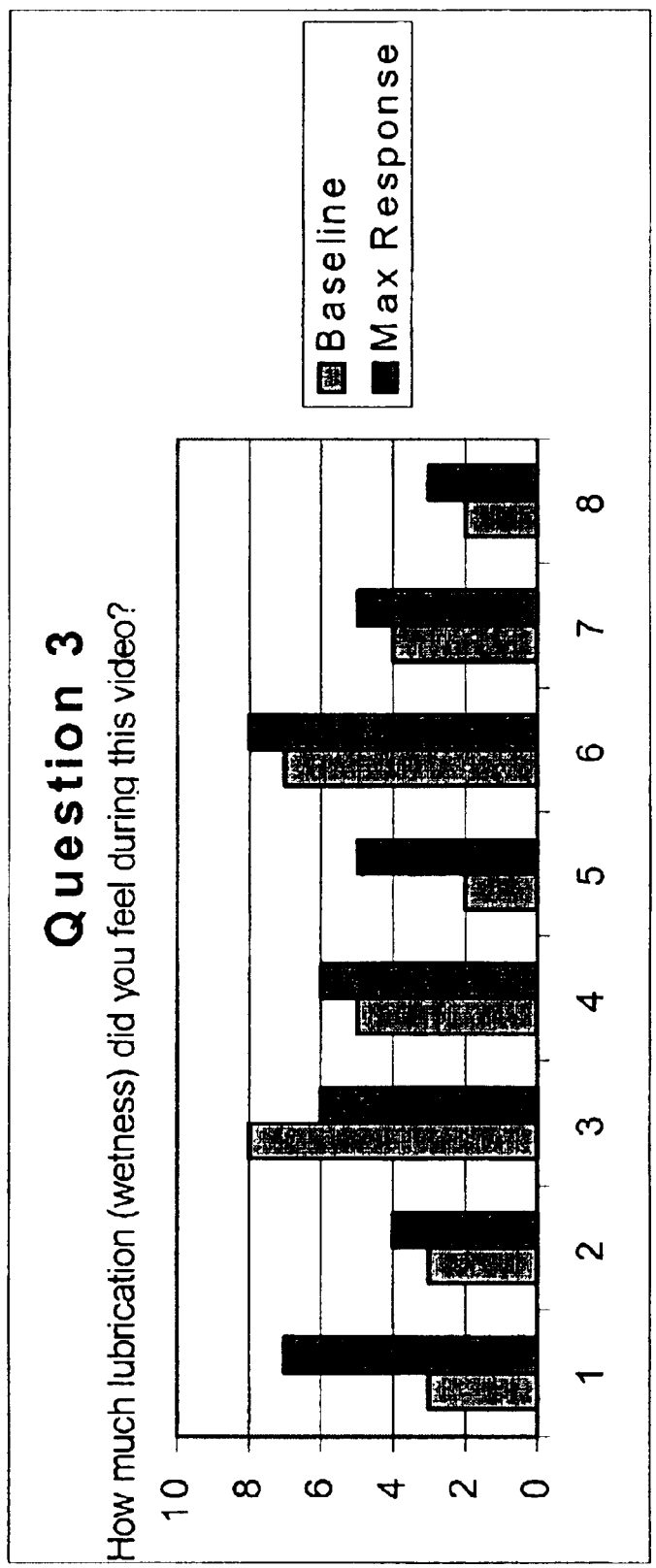
FIG. 6 is a graphical representation of the baseline responses and the maximum treatment responses to question 3 of the video assessment questionnaire.
Figure 7:
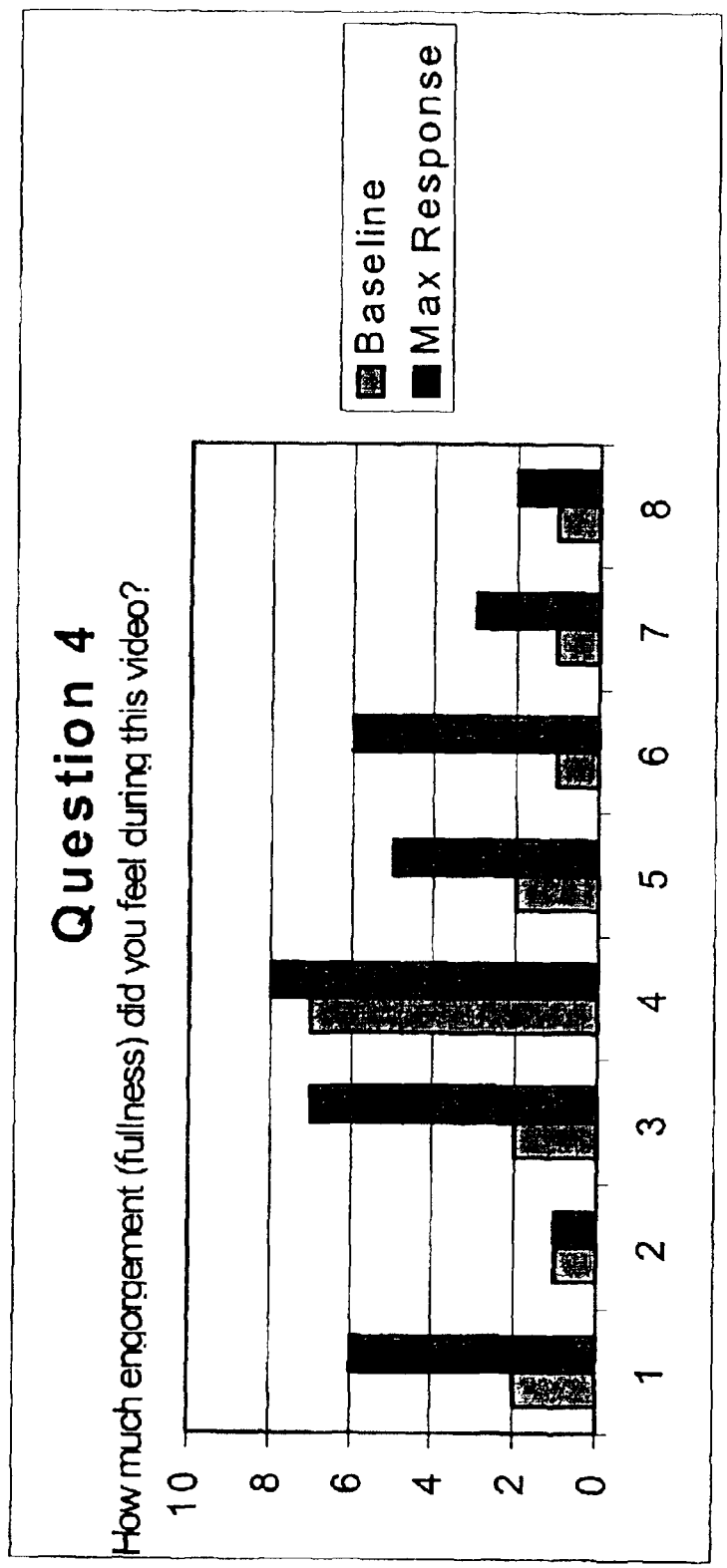
FIG. 7 is a graphical representation of the baseline responses and the maximum treatment responses to question 4 of the video assessment questionnaire.
Figure 8:
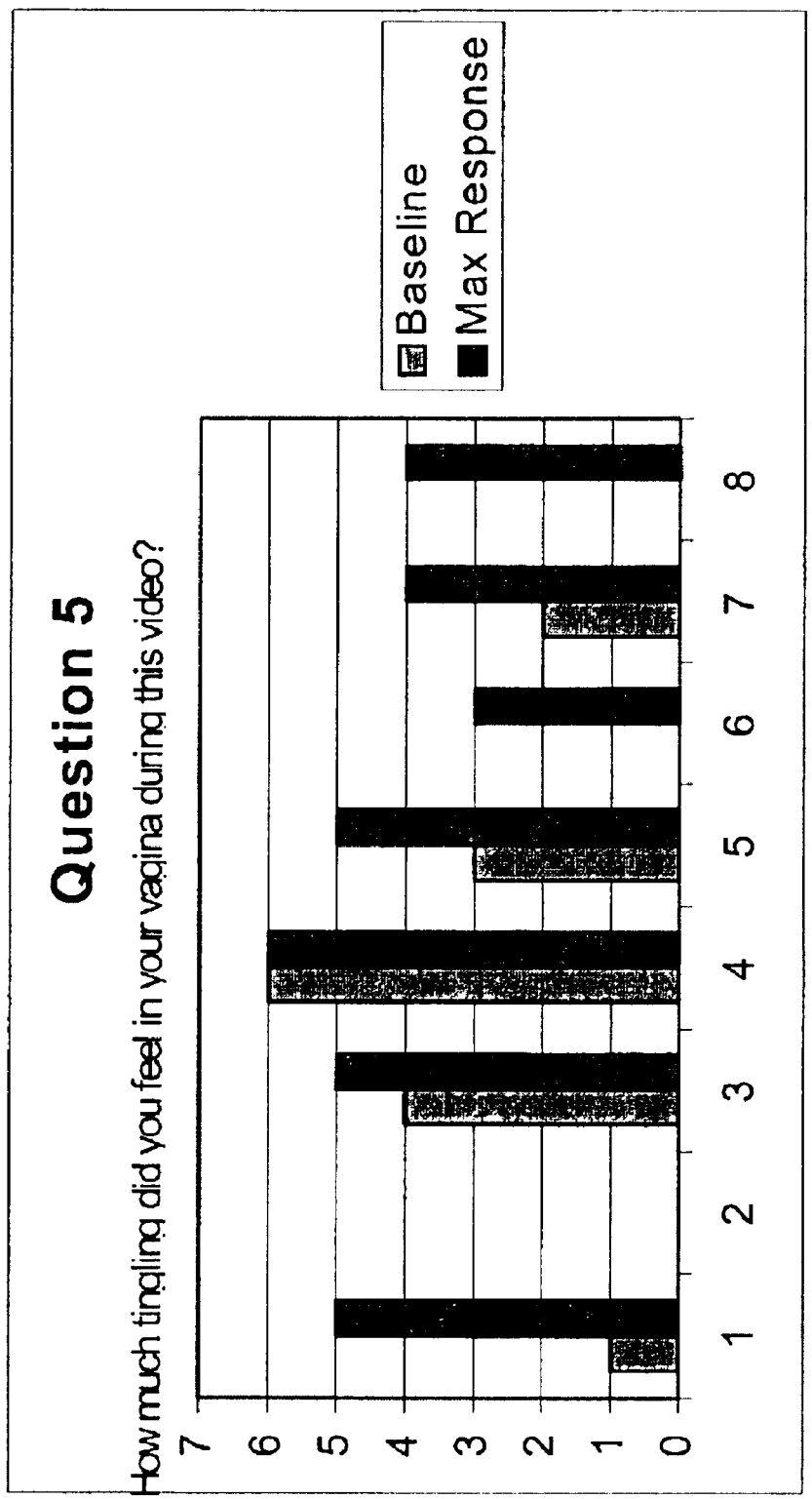
FIG. 8 is a graphical representation of the baseline responses and the maximum treatment responses to question 5 of the video assessment questionnaire.
Figure 9:
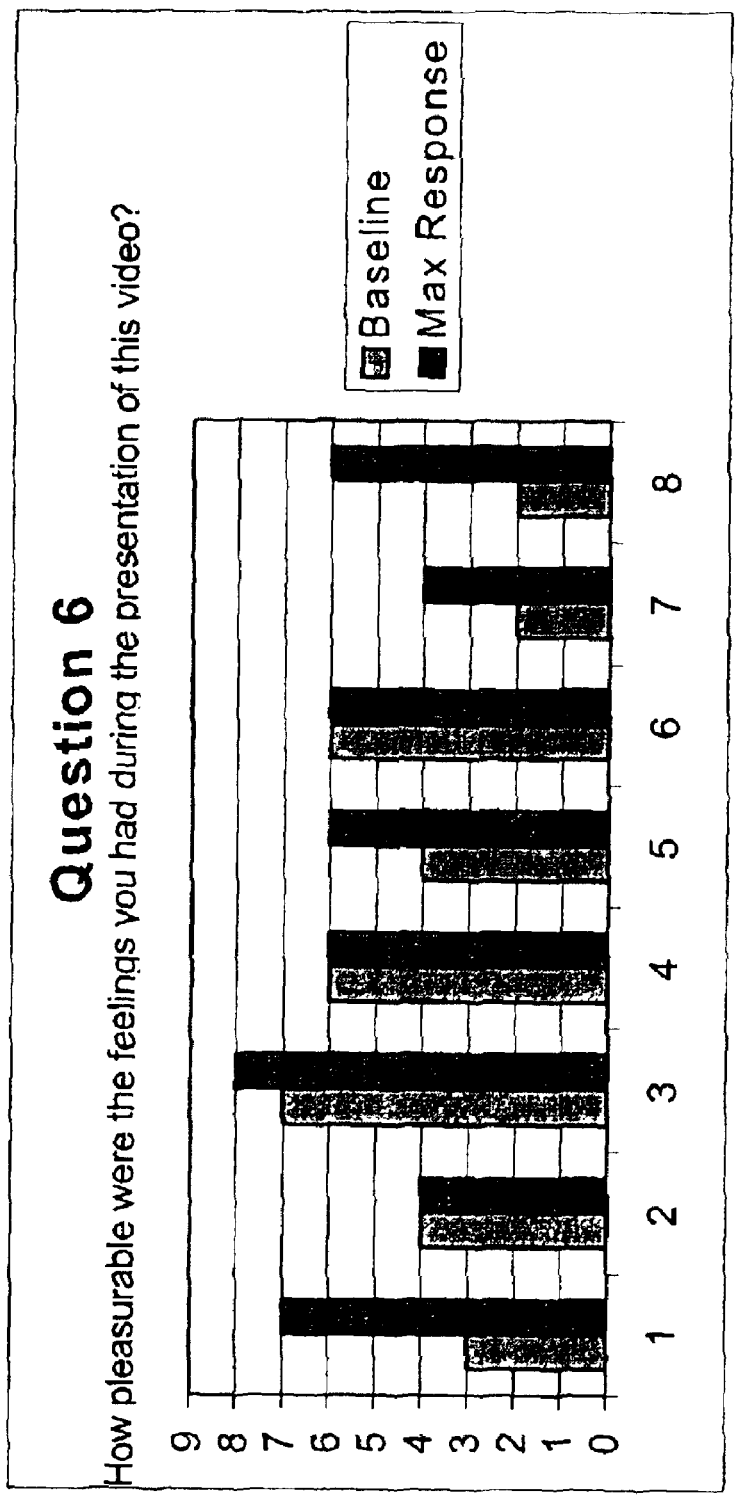
FIG. 9 is a graphical representation of the baseline responses and the maximum treatment responses to question 6 of the video assessment questionnaire.
Figure 10:
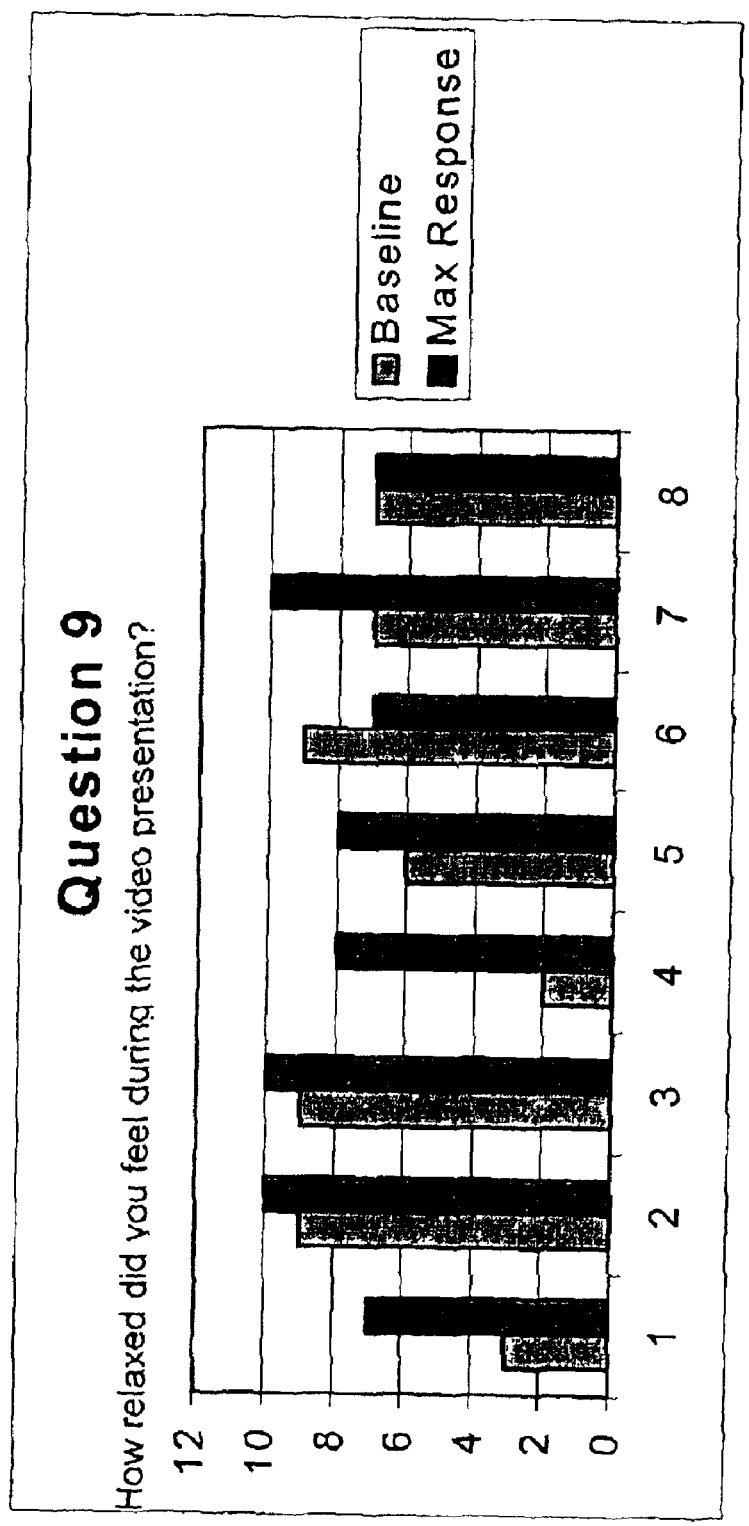
FIG. 10 is a graphical representation of the baseline responses and the maximum treatment responses to question 9 of the video assessment questionnaire.

*Mean of the difference between pre-treatment and post-treatment, using paired t-tests.
**Mean of the pre- to post-treatment change at each active drug visit, correcting for the change during treatment with PGE 0.05%.
***Standard error As with the vaginal blood flow measurements, the responses to the video assessment questionnaire showed high baseline responses (e.g., Table 9). The differences in responses between the lowest dose of PGE and the two higher doses are significant for question 3 (related to lubrication (Table 11) and engorgement at the highest dose level (Q4, Table 11). The graphs of the maximum responses show increased responses relative to baseline in all but one subject (FIGS. 6, 7). The responses to questions 2 (subjective arousal) and 6 (pleasurable feelings) are near the p=0.05 level if the 0.05% and 0.2% dose levels are compared (Table 11, compare to FIGS. 5, 9).

TABLE 9

VIDEO ASSESSMENT QUESTIONNAIRE RESULTS
Visit Means

|  | Q2 | Q3 | Q4 | Q5 | Q6 | Q9 |
|---|---|---|---|---|---|---|
| Placebo (N = 8) | 4.13 ± 1.6* | 4.25 ± 2.3 | 2.13 ± 2.0 | 2.00 ± 2.2 | 4.25 ± 1.9 | 6.50 ± 2.7 |
| $PGE_1$ 0.05% (N = 8) | 2.25 ± 1.9 | 2.25 ± 1.7 | 1.38 ± 2.2 | 2.00 ± 2.3 | 2.75 ± 2.1 | 7.50 ± 1.5 |
| $PGE_1$ 0.1% (N = 8) | 4.13 ± 1.7 | 3.88 ± 1.9 | 2.88 ± 2.7 | 2.38 ± 2.3 | 3.88 ± 2.1 | 7.75 ± 1.8 |
| $PGE_1$ 0.2% (N = 7) | 4.57 ± 1.7 | 4.43 ± 2.5 | 3.71 ± 2.4 | 3.29 ± 1.8 | 5.00 ± 1.9 | 8.00 ± 2.2 |

*Standard deviation

TABLE 10

VIDEO ASSESSMENT QUESTIONNAIRE RESULTS
Means of Within-Subject Differences Between Placebo and Treatment

|  | Q2 | Q3 | Q4 | Q5 | Q6 | Q9 |
|---|---|---|---|---|---|---|
| Placebo vs. $PGE_1$ 0.05% (N = 8) | −1.88 ± 1.1* (p = 0.13) | −2.00 ± 1.2 (p = 0.13) | −0.75 ± 1.1 (p = 0.52) | 0 ± 1.2 (p = 1.0) | −1.50 ± 1.3 (p = 0.27) | 1.00 ± 0.62 (p = 0.15) |
| Placebo vs. $PGE_1$ 0.1% (N = 8) | 0 ± 0.8 (p = 1.0) | −0.38 ± 1.0 (p = 0.73) | 0.75 ± 0.5 (p = 0.20) | 0.38 ± 0.8 (p = 0.64) | −0.38 ± 1.0 (p = 0.73) | 1.25 ± 1.0 (p = 0.27) |
| Placebo vs. $PGE_1$ 0.2% (N = 7) | 0.29 ± 0.4 (p = 0.46) | 0 ± 0.5 (p = 1.0) | 1.57 ± 1.0 (p = 0.17) | 1.14 ± 0.5 (p = 0.07) | 0.57 ± 0.5 (p = 0.32) | 1.00 ± 1.0 (p = 0.38) |

*Standard error

TABLE 11

VIDEO ASSESSMENT QUESTIONNAIRE
Means of Within-Subject Differences Between PGE$_1$ 0.05% and Treatment

|  | Q2 | Q3 | Q4 | Q5 | Q6 | Q9 |
|---|---|---|---|---|---|---|
| PGE$_1$ 0.05% vs. PGE$_1$ 0.1% (N = 8) | 1.88 ± 0.8* (p = 0.054) | 1.63 ± 0.7 (p = .04) | 1.50 ± 1.0 (p = 0.18) | 0.38 ± 0.7 (p = 0.62) | 1.13 ± 0.8 (p = 0.22) | 0.25 ± 0.6 (p = 0.68) |
| PGE$_1$ 0.05% vs. PGE$_1$ 0.2% (N = 7) | 2.57 ± 1.1 (p = 0.06) | 2.57 ± 1.0 (p = .04) | 3.00 ± 1.2 (p = .04) | 1.71 ± 1.0 (p = 0.14) | 2.57 ± 1.2 (p = 0.08) | 0.29 ± 0.6 (p = 0.65) |

*Standard error

TABLE 12

VITAL SIGNS
Means at Admission and Discharge at Each Visit

|  | PLACEBO (Visit 2) N = 8 | PGE$_1$ 0.05% (Visit 3) N = 8 | PGE$_1$ 0.1% (Visit 4) N = 8 | PGE$_1$ 0.2% (Visit 5) N = 7 |
|---|---|---|---|---|
| Standing Systolic | | | | |
| Admission | 108.8 ± 11.5** | 107.5 ± 12.6 | 103.0 ± 5.0 | 106.5 ± 7.8 |
| Discharge | 110.0 ± 11.3 | 103.5 ± 11.5 | 103.5 ± 11.4 | 104.0 ± 10.6 |
| Diastolic | | | | |
| Admission | 70.8 ± 5.8 | 70.8 ± 6.9 | 69.5 ± 7.2 | 71.0 ± 5.1 |
| Discharge | 72.3 ± 6.5 | 66.0 ± 7.3 | 68.8 ± 4.4 | 68.6 ± 4.1 |
| Pulse | | | | |
| Admission | 74.0 ± 5.1 | 75.0 ± 7.3 | 70.5 ± 5.7 | 77.3 ± 8.6 |
| Discharge | 72.3 ± 4.3 | 69.8 ± 5.5 | 69.8 ± 4.2 | 73.4 ± 8.0 |
| Supine Systolic | | | | |
| Admission | 110.5 ± 8.5 | 108.8 ± 6.0 | 110.5 ± 11.4 | 107.8 ± 10.8 |
| Discharge | 105.5 ± 6.7 | 102.5 ± 11.2 | 106.8 ± 9.9 | 108.6 ± 10.8 |
| Diastolic | | | | |
| Admission | 69.3 ± 6.0 | 69.8 ± 3.1 | 67.8 ± 6.5 | 67.3 ± 6.9 |
| Discharge | 67.0 ± 4.5 | 65.3 ± 7.1 | 68.3 ± 5.2 | 68.9 ± 5.0 |
| Pulse | | | | |
| Admission | 70.3 ± 7.5 | 71.5 ± 6.7 | 72.8 ± 4.7 | 75.5 ± 10.9 |
| Discharge | 68.8 ± 4.7 | 66.8 ± 5.4 | 68.3 ± 5.9 | 72.6 ± 7.4 |

**Standard deviation

TABLE 13

VITAL SIGNS
Means of Within-Subject Differences Between
Pre-Treatment and Post-Treatment at Each Visit

|  | PLACEBO (Visit 2) N = 8 | PGE$_1$ 0.05% (Visit 3) N = 8 | PGE$_1$ 0.1% (Visit 4) N = 8 | PGE$_1$ 0.2% (Visit 5) N = 7 |
|---|---|---|---|---|
| Standing | | | | |
| Systolic | 1.25 ± 3.0* (p = 0.68) | −4.00 ± 4.3 (p = 0.39) | 0.50 ± 4.7 (p = 0.92) | −4.57 ± 4.2 (p = 0.32) |
| Diastolic | 1.50 ± 1.8 (p = 42) | −4.75 ± 3.5 (p = 0.22) | −0.75 ± 3.0 (p = 0.81) | −3.71 ± 2.3 (p = 0.16) |
| Pulse | −1.75 ± 2.7 (p = 0.54) | −5.25 ± 2.7 (p = 0.09) | −0.75 ± 2.6 (p = 0.78) | −5.71 ± 2.7 (p = 0.08) |
| Supine | | | | |
| Systolic | −5.00 ± 2.2 (p = 0.055) | −6.25 ± 2.9 (p = 0.07) | −3.75 ± 3.9 (p = 0.37) | −0.57 ± 4.0 (p = 0.89) |
| Diastolic | −2.25 ± 1.2 (p = 0.11) | −4.50 ± 2.5 (p = 0.11) | 0.50 ± 1.9 (p = 0.80) | 0.57 ± 3.5 (p = 0.88) |
| Pulse | −1.50 ± 3.7 (p = 0.70) | −4.75 ± 2.7 (p = 0.12) | −4.50 ± 2.2 (p = 0.08) | −4.86 ± 3.4 (p = 0.20) |

*Standard error

The minimal adverse events and the comparison of vital signs (Tables 13 and 14) indicated that the medication was well tolerated.

The raw data presented graphically in FIGS. 4–10 are presented in Table 14, below. Baseline response levels were recorded following the administration of placebo (visit 2). Maximum response levels were recorded following the administration of PGE$_1$ at 0.05%, 0.1% or 0.2% (visits 3–5). For all questions, the maximum responses showed increased means compared to baseline means (Table 14, bottom row).

The results of analysis of the raw data of Table 14 are presented in Table 15, below, where statistical significance at the p<0.05 level is designated by "*" and at the p<0.01 level by "**". All statistical analysis of the difference between the mean baseline value and the mean maximum response were performed by paired t test with two-tailed P value as described in Bancroft, H.; 1957, Introduction to Biostatistics, 172–182.

The increases in maximum response means compared to baseline means were statistically significant for Questions No. 2, No. 4, No. 5, and No. 6 as shown in Table 15. These results indicate that PGE$_1$ treatment significantly increased female sexual response including subjective arousal, engorgement, vaginal tingling, and pleasurable feelings. The significant (p<0.05) response to question No. 2, "How much subjective arousal did you have during this video?", shows that the method of the invention is effective in increasing subjective arousal in even this small sample of treated patients. The significant (p<0.01) response to question No.

4, "How much engorgement (fullness) did you feel during this video?", shows that the method of the invention is effective in subjective awareness of increased engorgement in even this small sample of treated patients. The significant ($p<0.01$) response to question No. 5, "How much vaginal tingling did you feel during this video?", shows that the method of the invention is effective in increasing subjective awareness of increase vaginal tingling in even this small sample of treated patients. The significant ($p<0.05$) response to question No. 6, "How pleasurable were the feelings you had during the presentation of this video?", shows that the method of the invention is effective in increasing subjective pleasurable feelings in even this small sample of treated patients. These data thus show significant increases in subjective aspects that are specific to female sexual arousal disorder.

TABLE 14

Questionnaire Response Raw Data

| Patient No. | Question #2 | | Question #3 | | Question #4 | | Question #5 | | Question #6 | | Question #9 | |
|---|---|---|---|---|---|---|---|---|---|---|---|---|
| | Base-line | Max. Resp. | Base-Line | Max. Resp. | Base-line | Max. Resp. | Base-line | Max. Resp. | Base-line | Max. Resp. | Base-line | Max. Resp. |
| 1 | 3 | 7 | 3 | 7 | 2 | 6 | 1 | 5 | 3 | 7 | 3 | 7 |
| 2 | 3 | 4 | 3 | 4 | 1 | 1 | 0 | 0 | 4 | 4 | 9 | 10 |
| 3 | 6 | 7 | 8 | 6 | 2 | 7 | 4 | 5 | 7 | 8 | 9 | 10 |
| 4 | 7 | 6 | 5 | 6 | 7 | 8 | 6 | 6 | 6 | 6 | 2 | 8 |
| 5 | 3 | 5 | 2 | 5 | 2 | 5 | 3 | 5 | 4 | 6 | 6 | 8 |
| 6 | 4 | 5 | 7 | 8 | 1 | 6 | 0 | 3 | 6 | 6 | 9 | 7 |
| 7 | 4 | 5 | 4 | 5 | 1 | 3 | 2 | 4 | 2 | 4 | 7 | 10 |
| 8 | 3 | 5 | 2 | 3 | 1 | 2 | 0 | 4 | 2 | 6 | 7 | 7 |
| Mean | 4.1 | 5.5 | 4.3 | 5.5 | 2.1 | 4.8 | 2.0 | 4.0 | 4.3 | 5.9 | 6.5 | 8.4 |

TABLE 15

Statistical Analysis of Responses (p value)

| Question #2 | Question #3 | Question #4 | Question #5 | Question #6 | Question #9 |
|---|---|---|---|---|---|
| P = 0.028* | P = 0.0835 | P = 0.0062** | P = 0.0096** | P = 0.0284* | P = 0.0693 |

Statistical significance at the $p < 0.05$ level is designated by "*" and at the $p < 0.01$ level by "**".

We claim:

1. A method for ameliorating female sexual arousal disorder, comprising the step of administering a composition to the genitalia of a human female in need of treatment, the composition comprising:
   an amount of a vasoactive prostaglandin effective to produce an increase in sexual arousal;
   a shear-thinning polysaccharide gum;
   a lipophilic component chosen from the group consisting of an aliphatic $C_1$ to $C_8$ alcohol, an aliphatic $C_8$ to $C_{30}$ ester, and mixtures thereof;
   a penetration enhancer chosen from the group consisting of alkyl-2-(N-substituted amino) alkanoates, (N-substituted amino) alkanol alkanoates, pharmaceutically acceptable salts thereof and mixtures thereof;
   water; and
   an acidic buffer system that provides a buffered pH of about 3.0 to about 7.4,
   wherein treatment increases subjective sexual arousal thereby alleviating symptoms of female sexual arousal disorder, wherein female sexual arousal disorder is the persistent or recurrent inability to attain, or to maintain, sufficient sexual excitement, which causes personal distress.

2. The method in accordance with claim 1, wherein the vasoactive prostaglandin is selected from the group consisting of $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_3$ and mixtures thereof.

3. The method in accordance with claim 1, wherein the shear-thinning polysaccharide gum is a modified galactomannan gum.

4. The method in accordance with claim 3, wherein the modified galactomannan gum is a modified guar gum.

5. The method in accordance with claim 1, wherein the lipophilic compound is at least one aliphatic $C_8$ to $C_{30}$ ester.

6. The method in accordance with claim 1, wherein the lipophilic compound is at least one glyceryl ester selected from the group consisting monoglycerides, diglycerides, triglycerides, and mixtures thereof.

7. The method in accordance with claim 1, wherein the lipophilic compound is at least one glyceryl ester selected from the group consisting of glyceryl monooleate, triolein, trimyristin, tristearin, and mixtures thereof.

8. The method in accordance with claim 1, wherein the acidic buffer system provides a buffered pH value for said composition in the range of about 3 to about 6.0.

9. The method in accordance with claim 1, wherein the composition further comprises an emulsifier selected from the group consisting of sucrose esters, polyoxyethylene sorbitan esters, long chain alcohols, and glyceryl esters.

10. The method in accordance with claim 1, wherein the emulsifier is at least one glyceryl ester selected from the group consisting of glyceryl monoolcate, triolein, trimyristin, tristearin, and mixtures thereof.

11. The method in accordance with claim 1, wherein the composition further comprises a fragrance.

12. The method in accordance with claim 1, wherein the composition further comprises a preservative.

13. The method in accordance with claim 1, wherein the composition further comprises a topical anesthetic.

14. A method for ameliorating female sexual arousal disorder, comprising the step of applying a shear-thinning semi-solid prostaglandin composition to the genitalia of a human female in need of treatment, the composition comprising:

a modified polysaccharide gum;

a prostaglandin selected from the group consisting of $PGE_1$, pharmaceutically acceptable salts thereof, lower alkyl esters thereof and mixtures thereof;

about 0.5 percent to about 10 percent DDAIP or a pharmaceutically acceptable salt thereof, based on the total weight of the composition;

about 0.5 percent to about 10 percent, based on the total weight of the composition, of a lower alcohol selected from the group consisting of ethanol, propanol, isopropanol and mixtures thereof;

about 0.5 percent to about 10 percent of an ester selected from the group consisting of ethyl laurate, isopropyl myristate, isopropyl laurate and mixtures thereof, based on the total weight of the composition;

water; and an acidic buffer system that provides a buffered pH of about 3.0 to about 7.4, wherein treatment increases subjective sexual arousal thereby alleviating symptoms of female sexual arousal disorder, wherein female sexual arousal disorder is the persistent or recurrent inability to attain, or to maintain, sufficient sexual excitement, which causes personal distress.

15. The method in accordance with claim 14, further comprising an emulsifier selected from the group consisting of sucrose esters, polyoxyethylene sorbitan esters, long chain alcohols, and glyceryl esters.

16. The method in accordance with claim 15, wherein the emulsifier is a sucrose stearate.

17. The method in accordance with claim 15, wherein the emulsifier comprises at least one glyceryl ester selected from the group consisting of glyceryl monooleate, triolein, trimyristin, tristearin, and mixtures thereof.

18. The method in accordance with claim 14, wherein the composition further comprises a fragrance.

19. The method in accordance with claim 14 wherein the composition comprises a preservative.

20. The method in accordance with claim 14, wherein the composition further comprises a topical anesthetic.

21. A method for ameliorating female sexual arousal disorder, comprising the step of administering a shear-thinning semi-solid composition to the genitalia of a human female in need of treatment, the composition comprising:

an amount of a vasoactive prostaglandin effective to produce an increase in sexual arousal;

a polyacrylic polymer;

a lipophilic component chosen from the group consisting of an aliphatic $C_1$ to $C_8$ alcohol, an aliphatic $C_8$ to $C_{30}$ ester, and mixtures thereof;

a penetration enhancer chosen from the group consisting of alkyl-2-(N-substituted amino) alkanoates, (N-substituted amino) alkanol alkanoates, pharmaceutically acceptable salts thereof and mixtures thereof;

water; and an acidic buffer system that provides a buffered pH of about 3.0 to about 7.4, wherein treatment increases subjective sexual arousal thereby alleviating symptoms of female sexual arousal disorder, wherein female sexual arousal disorder is the persistent or recurrent inability to attain, or to maintain, sufficient sexual excitement, which causes personal distress.

22. The method in accordance with claim 21, wherein the vasoactive prostaglandin is selected from the group consisting of $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_3$ and mixtures thereof.

23. The method in accordance with claim 21, wherein the lipophilic compound is at least one aliphatic $C_8$ to $C_{30}$ ester.

24. The method in accordance with claim 21, wherein the lipophilic compound is at least one glyceryl ester selected from the group consisting monoglycerides, diglycerides, triglycerides, and mixtures thereof.

25. The method in accordance with claim 21, wherein the lipophilic compound is at least one glyceryl ester selected from the group consisting of glyceryl monooleate, triolein, trimyristin, tristearin, and mixtures thereof.

26. The method in accordance with claim 21, wherein the acidic buffer system provides a buffered pH value for said composition in the range of about 3 to about 6.0.

27. The method in accordance with claim 21, wherein the composition further comprises an emulsifier selected from the group consisting of sucrose esters, polyoxyethylene sorbitan esters, long chain alcohols, and glyceryl esters.

28. The method in accordance with claim 21, wherein the emulsifier is at least one glyceryl ester selected from the group consisting of glyceryl monooleate, triolein, trimyristin, tristearin, and mixtures thereof.

29. The method in accordance with claim 21, wherein the composition further comprises a fragrance.

30. The method in accordance with claim 21, wherein the composition further comprises a preservative.

31. The method in accordance with claim 21, wherein the composition further comprises a topical anesthetic.

* * * * *